US010933176B2

(12) United States Patent
Gavlak et al.

(10) Patent No.: US 10,933,176 B2
(45) Date of Patent: *Mar. 2, 2021

(54) MANIFOLD FOR MEDICAL WASTE COLLECTION DEVICE

(71) Applicant: Stryker Corporation, Kalamazoo, MI (US)

(72) Inventors: William Gavlak, Atlanta, GA (US); Richard Grambergs, Suwanee, GA (US); Michael A. Fisher, Lawrenceville, GA (US); Michael J. Glatzer, Atlanta, GA (US); Roland Krevitt, Scotts Valley, CA (US)

(73) Assignee: Stryker Corporation, Kalamazoo, MI (US)

( * ) Notice: Subject to any disclaimer, the term of this patent is extended or adjusted under 35 U.S.C. 154(b) by 301 days.

This patent is subject to a terminal disclaimer.

(21) Appl. No.: 15/791,278

(22) Filed: Oct. 23, 2017

(65) Prior Publication Data

US 2018/0064857 A1 Mar. 8, 2018

Related U.S. Application Data

(63) Continuation of application No. 15/143,212, filed on Apr. 29, 2016, now Pat. No. 9,795,723.
(Continued)

(51) Int. Cl.
*A61M 1/00* (2006.01)
*A61B 17/16* (2006.01)
*A61B 10/00* (2006.01)

(52) U.S. Cl.
CPC ....... *A61M 1/0056* (2013.01); *A61B 17/1635* (2013.01); *A61M 1/0049* (2013.01);
(Continued)

(58) Field of Classification Search
CPC .............. A61M 1/0056; A61M 1/0049; A61M 1/0088; A61M 1/0058; A61B 17/1635; A61B 10/0045; A61B 2010/0061
(Continued)

(56) References Cited

U.S. PATENT DOCUMENTS

D249,541 S   9/1978  Cattano, Sr.
4,411,783 A  10/1983 Dickens et al.
(Continued)

FOREIGN PATENT DOCUMENTS

EP   2388024 A1  11/2011
EP   2129948 B1   3/2013
(Continued)

OTHER PUBLICATIONS

International Preliminary Report on Patentability for International Application PCT/US2016/038541, Report dated Dec. 26, 2017, mailed Jan. 4, 2018, 4 Pgs.
(Continued)

*Primary Examiner* — Andrew J Mensh
(74) *Attorney, Agent, or Firm* — Howard & Howard Attorneys PLLC

(57) ABSTRACT

Medical waste collection manifolds that that may connect to a vacuum system to create suction, such that liquid, semi-solid, or solid biological or medical waste may be collected are provided. The manifold may be configured to collect hazardous waste in a manner to ensure proper containment.

20 Claims, 35 Drawing Sheets

Related U.S. Application Data

(60) Provisional application No. 62/183,128, filed on Jun. 22, 2015, provisional application No. 62/239,646, filed on Oct. 9, 2015.

(52) U.S. Cl.
CPC ....... *A61M 1/0088* (2013.01); *A61B 10/0045* (2013.01); *A61B 2010/0061* (2013.01); *A61M 1/0058* (2013.01)

(58) Field of Classification Search
USPC .......................................................... 604/321
See application file for complete search history.

(56) References Cited

U.S. PATENT DOCUMENTS

| | | |
|---|---|---|
| 4,495,072 A | 1/1985 | Fields |
| 4,588,426 A | 5/1986 | Virgille et al. |
| 4,655,754 A | 4/1987 | Richmond et al. |
| 4,870,961 A | 10/1989 | Barnard et al. |
| 4,946,434 A | 8/1990 | Plaisted et al. |
| 5,242,434 A | 9/1993 | Terry |
| 5,254,086 A | 10/1993 | Palmer et al. |
| D342,306 S | 12/1993 | Young |
| 5,464,391 A | 11/1995 | DeVale |
| 5,556,261 A | 9/1996 | Kimura et al. |
| 5,562,614 A | 10/1996 | O'Donnell |
| 5,637,103 A | 6/1997 | Kerwin et al. |
| 5,725,516 A * | 3/1998 | Cook ................ A61M 1/0001 600/581 |
| 5,792,126 A | 8/1998 | Tribastone et al. |
| 5,997,733 A | 12/1999 | Wilbur et al. |
| 6,027,490 A | 2/2000 | Radford et al. |
| 6,061,855 A | 5/2000 | Flick |
| 6,079,070 A | 6/2000 | Flick et al. |
| 6,083,205 A | 7/2000 | Bourne et al. |
| 6,099,511 A | 8/2000 | Devos et al. |
| 6,180,000 B1 | 1/2001 | Wilbur et al. |
| 6,222,283 B1 | 4/2001 | Regla |
| 6,273,296 B1 | 8/2001 | Brown |
| 6,331,246 B1 | 12/2001 | Beckham et al. |
| 6,375,625 B1 | 4/2002 | French et al. |
| 6,488,675 B1 | 12/2002 | Radford et al. |
| 6,733,664 B2 | 5/2004 | Menne et al. |
| 6,893,425 B2 | 5/2005 | Dunn et al. |
| 6,902,673 B2 | 6/2005 | Smit et al. |
| 6,918,893 B2 | 7/2005 | Houde et al. |
| 6,935,459 B2 | 8/2005 | Austin et al. |
| 6,951,228 B2 | 10/2005 | Steigerwalt et al. |
| 7,132,045 B1 * | 11/2006 | Trangsrud ................. E03F 1/00 210/163 |
| 7,163,618 B2 | 1/2007 | Beckham et al. |
| 7,172,572 B2 | 2/2007 | Diamond et al. |
| 7,263,734 B1 | 9/2007 | Buchanan et al. |
| 7,497,340 B2 | 3/2009 | Hershberger et al. |
| 7,513,890 B2 | 4/2009 | Usher et al. |
| 7,615,037 B2 | 11/2009 | Murray et al. |
| 7,621,898 B2 | 11/2009 | Lalomia et al. |
| 8,025,173 B2 | 9/2011 | Michaels |
| 8,088,291 B2 | 1/2012 | Hershberger et al. |
| 8,104,125 B2 | 1/2012 | Soltani et al. |
| 8,172,817 B2 | 5/2012 | Michaels et al. |
| 8,187,534 B2 | 5/2012 | Mao |
| 8,216,199 B2 | 7/2012 | Murray et al. |
| 8,292,857 B2 | 10/2012 | Martini et al. |
| D678,502 S | 3/2013 | Schmidt et al. |
| D678,503 S | 3/2013 | Schmidt et al. |
| 8,424,685 B2 | 4/2013 | Smit et al. |
| 8,449,510 B2 | 5/2013 | Martini et al. |
| 8,478,385 B2 | 7/2013 | Liu et al. |
| 8,518,002 B2 | 8/2013 | Murray et al. |
| 8,827,969 B2 | 9/2014 | Martini et al. |
| 8,915,897 B2 | 12/2014 | Murray |
| 8,920,394 B2 | 12/2014 | Smith et al. |
| 9,056,158 B2 | 6/2015 | Gavlak et al. |
| 9,089,629 B2 | 7/2015 | Martini et al. |
| 9,089,801 B1 | 7/2015 | Gavlak et al. |
| 9,795,723 B2 | 10/2017 | Gavlak et al. |
| 2003/0181850 A1 | 9/2003 | Diamond et al. |
| 2004/0016691 A1 | 1/2004 | Smit et al. |
| 2004/0163884 A1 | 8/2004 | Austin et al. |
| 2005/0139532 A1 | 6/2005 | Hershberger et al. |
| 2005/0171495 A1 | 8/2005 | Austin et al. |
| 2005/0189283 A1 | 9/2005 | Smit et al. |
| 2005/0189288 A1 * | 9/2005 | Hershberger ....... A61M 1/0056 210/448 |
| 2006/0236913 A1 | 10/2006 | Wills |
| 2007/0135778 A1 * | 6/2007 | Murray ................ A61B 50/13 604/317 |
| 2008/0053539 A1 | 3/2008 | Hershberger et al. |
| 2009/0106906 A1 | 4/2009 | Soltani et al. |
| 2009/0159535 A1 | 6/2009 | Hershberger et al. |
| 2009/0204078 A1 | 8/2009 | Mitchell et al. |
| 2010/0282666 A1 | 11/2010 | Smit et al. |
| 2010/0297577 A1 | 11/2010 | Cohen |
| 2011/0277851 A1 | 11/2011 | Martini et al. |
| 2011/0278296 A1 | 11/2011 | Martini |
| 2012/0111778 A1 | 5/2012 | Gavlak et al. |
| 2013/0067662 A1 | 3/2013 | Jusiak et al. |
| 2013/0206670 A1 | 8/2013 | Smit et al. |
| 2013/0292319 A1 | 11/2013 | Fulkerson et al. |
| 2013/0345652 A1 | 12/2013 | Murray et al. |
| 2014/0130937 A1 | 5/2014 | Harshman et al. |
| 2014/0323914 A1 * | 10/2014 | VanderWoude .... A61M 1/0058 600/582 |
| 2014/0336599 A1 | 11/2014 | Patel et al. |
| 2014/0338529 A1 | 11/2014 | Reasoner et al. |
| 2014/0343515 A1 | 11/2014 | Sylvester et al. |
| 2015/0011953 A1 | 1/2015 | Schmidt |
| 2015/0105740 A1 | 4/2015 | Reasoner et al. |
| 2016/0367734 A1 | 12/2016 | Gavlak et al. |

FOREIGN PATENT DOCUMENTS

| | | |
|---|---|---|
| GB | 1253516 A | 11/1971 |
| GB | 2488707 A | 9/2012 |
| WO | 2005042061 A1 | 5/2005 |
| WO | 2016209820 | 12/2016 |

OTHER PUBLICATIONS

International Search Report and Written Opinion for International Application No. PCT/US2016/038541, completed Aug. 17, 2016, dated Sep. 13, 2016, 5 Pgs.

* cited by examiner

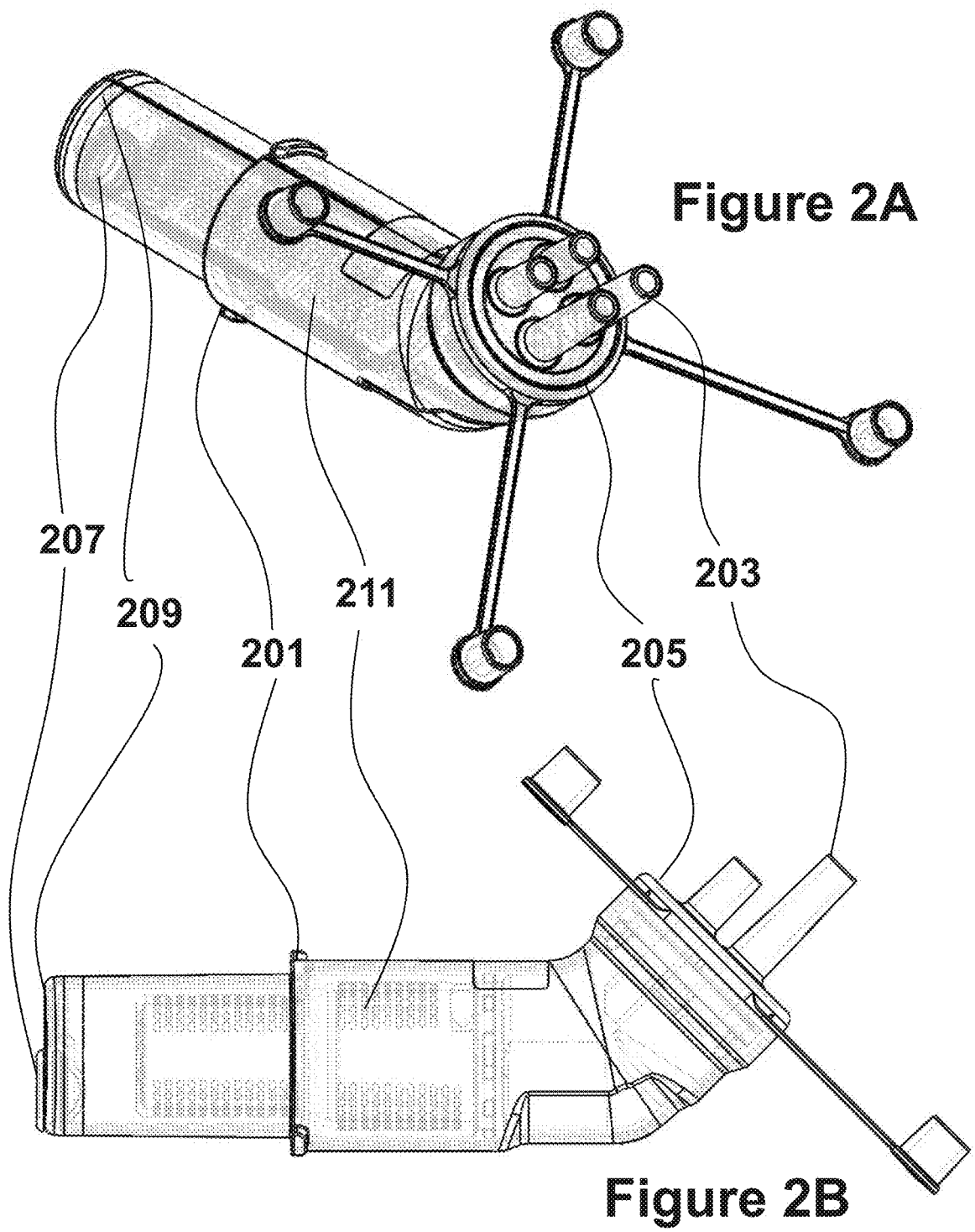

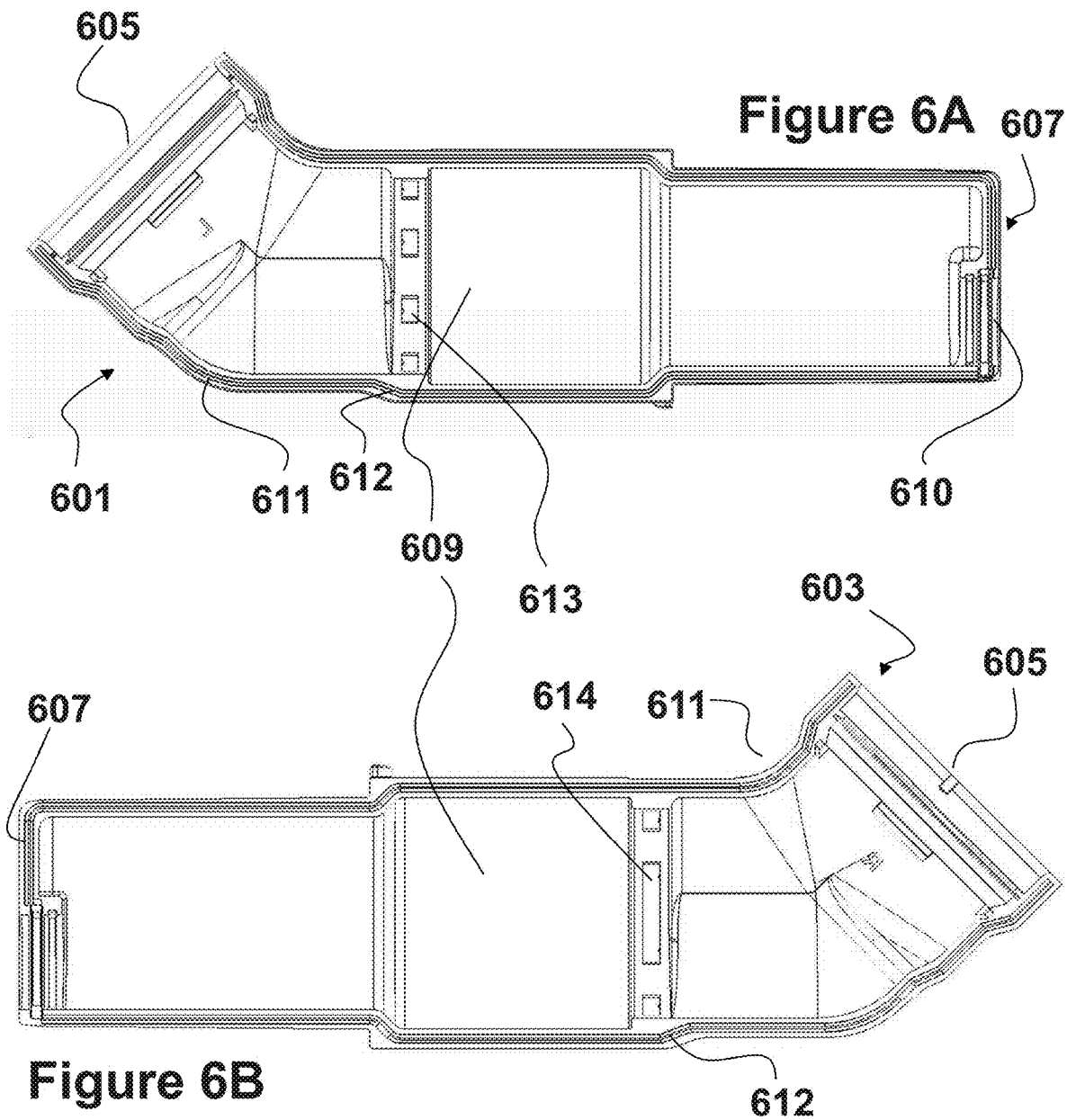

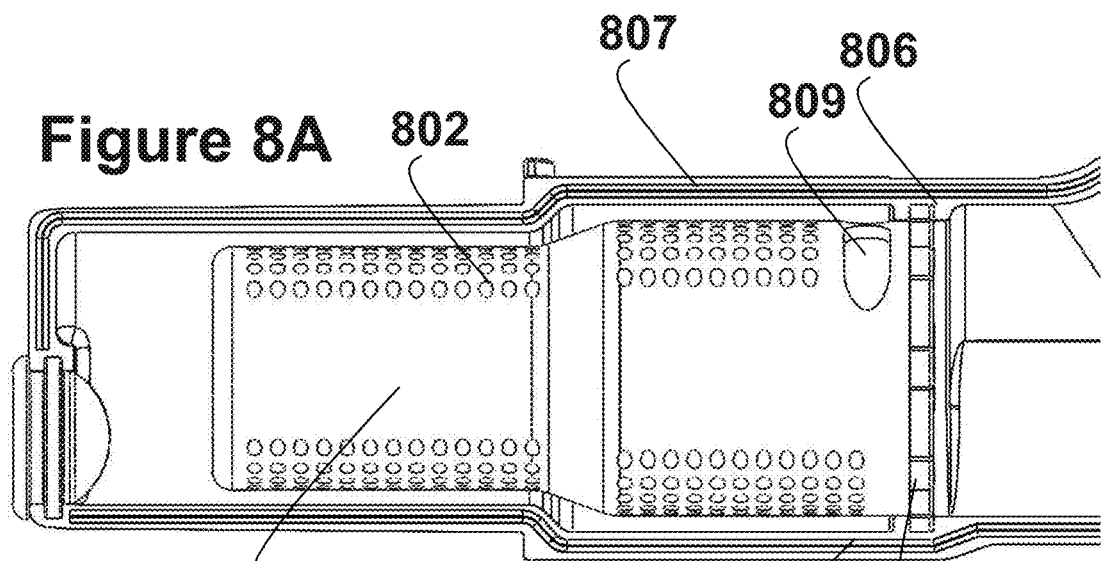
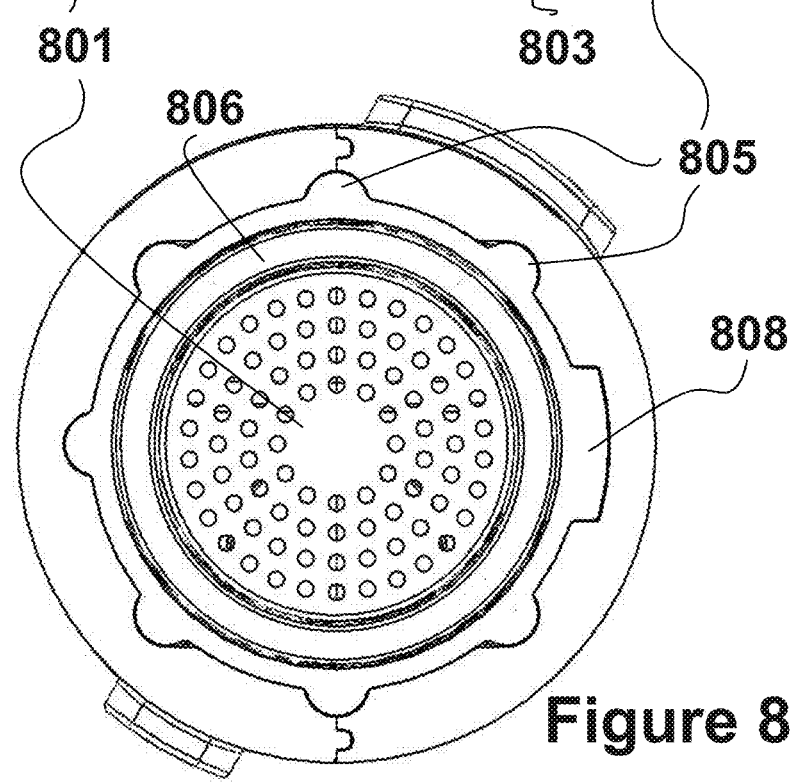

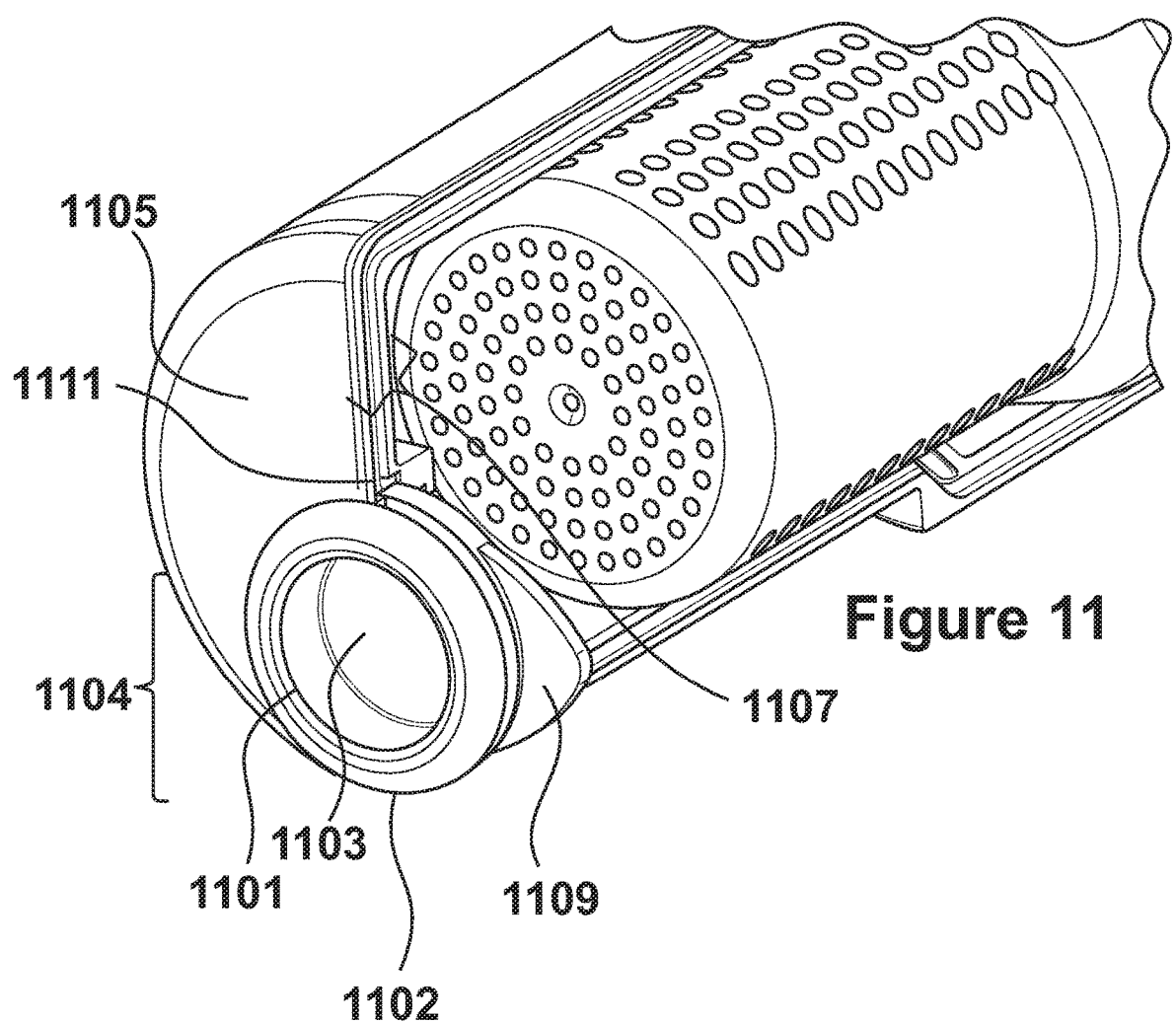

Fig. 12
Figure 12A
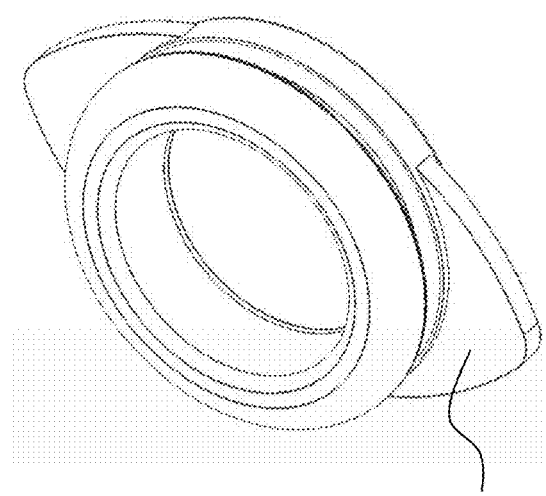
1201
Figure 12B
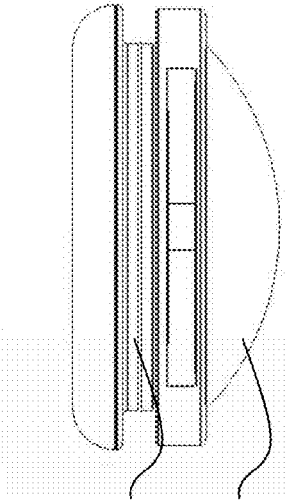
1202  1203
Figure 12C
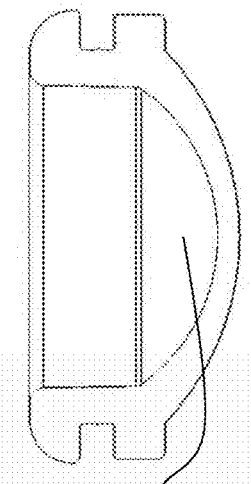
1205
Figure 12D
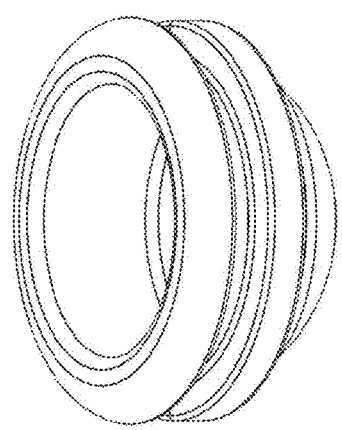
Figure 12E
1207

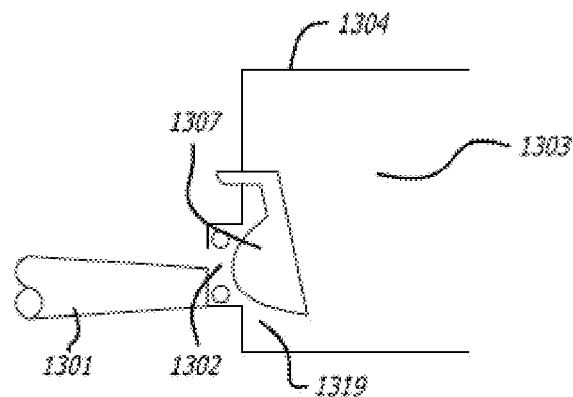
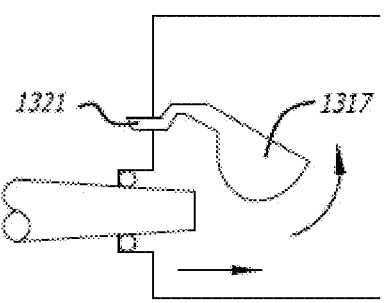
Figure 13D
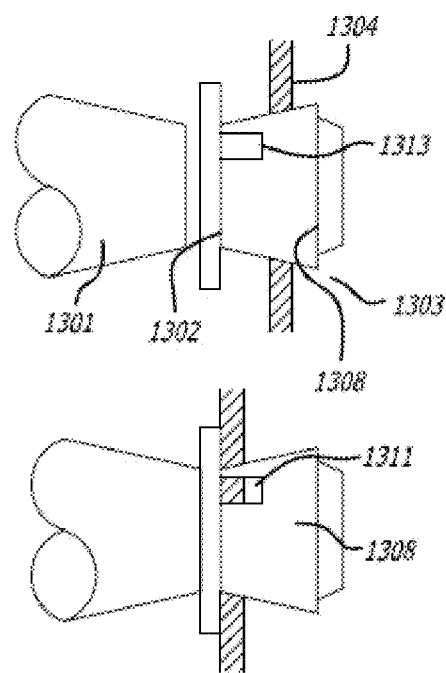
Figure 13E

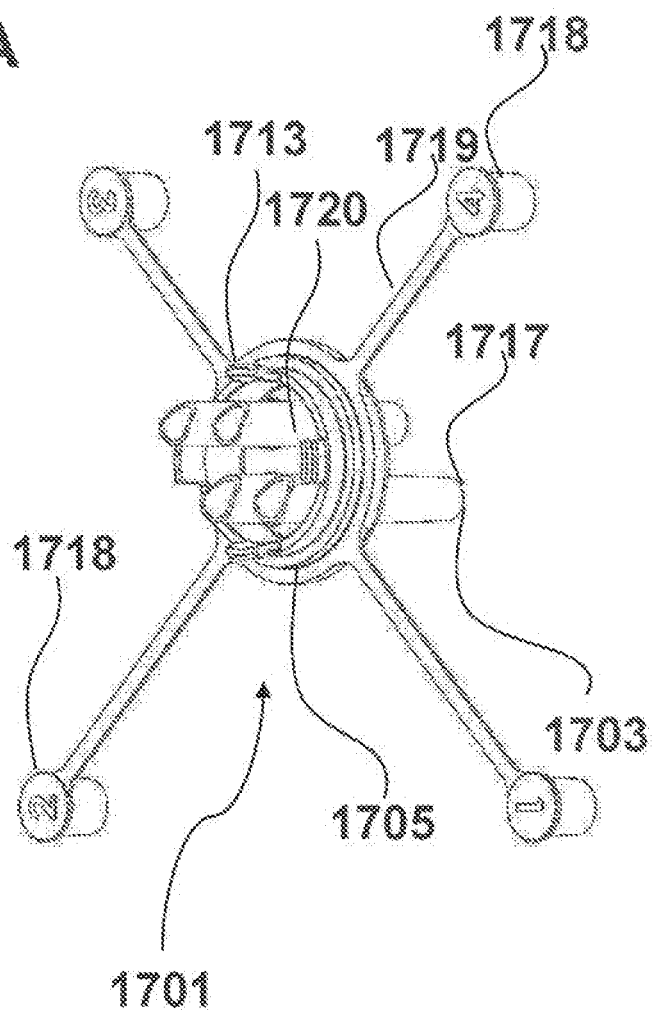

2111

MANIFOLD FOR MEDICAL WASTE COLLECTION DEVICE

CROSS-REFERENCE TO RELATED APPLICATIONS

The current application is a continuation of U.S. application Ser. No. 15/143,212, filed Apr. 29, 2016, which application claims priority to U.S. Provisional Application No. 62/183,128, filed Jun. 22, 2015 and to U.S. Provisional Application No. 62/239,646, filed Oct. 9, 2015, the disclosures of which are incorporated herein by reference in their entirety.

FIELD OF THE INVENTION

The current invention is related to a device to collect biological waste; and particularly to a manifold that may collect solid and/or semi-solid medical waste during medical procedures.

BACKGROUND OF THE INVENTION

Medical procedures, especially surgeries, generate biological and other waste. The waste can constitute a mixture of solids, semi-solids, and liquids, all of which must be collected in a manner that minimizes hazards, such as waste release into the environment. A common way to extract the medical waste is to use a vacuum to draw the waste away from the source. Accumulating the waste within a safe, hazard-preventing manifold is necessary for proper disposal.

SUMMARY OF THE INVENTION

The current invention is directed to a manifold device that collects solid and semi-solid medical waste when attached to a vacuum body, the device being used during medical procedures that require collection of medical waste by means of suction.

Many embodiments are directed to a manifold for connection to a waste collection vacuum device, including:
- a manifold body having proximal and distal ends and defining an internal volume providing a fluid path therebetween, and wherein the manifold body has an angular bend disposed along the length thereof, such that the proximal end lies along a first longitudinal axis and the distal end lies along a second longitudinal axis, and wherein the first and second longitudinal axes are angularly offset;
- a suction port assembly disposed within the proximal end of the manifold body, and providing at least one suction port providing a fluid path into the internal volume of the manifold body;
- a vacuum port disposed within the distal end of the manifold body, and providing at least one fluid outlet from the internal volume of the manifold body, the vacuum port being configured to receive a vacuum inlet integral with the vacuum device;
- a filter element secured within the internal volume of the manifold body such that the fluid path between the proximal and distal ends passes therethrough;
- at least one orientation feature disposed on the outer surface of the manifold body and configured to affix the manifold body within the vacuum device and fix the orientation of the manifold body relative to the vacuum device; and
- wherein the manifold body and at least one orientation feature are configured such that when the manifold body is affixed within the vacuum device the at least one suction port disposed in the proximal end of the manifold body is angled upward relative to the direction of gravity.

In other embodiments the angular offset is greater than 25° and less than 90°.

In still other embodiments the angular bend is greater than 30° and less than 60°.

In yet other embodiments the angular bend is about 45°.

In still yet other embodiments the angular bend offsets the suction port from the fluid path disposed along the second longitudinal axis of the manifold body sufficiently to prevent reflux of a liquid waste back through the suction port.

In still yet other embodiments the filter element is a basket disposed along the second longitudinal axis and containing a plurality of apertures having at least a first aperture dimension, the plurality of apertures forming a portion of the fluid path through the manifold body. In many such embodiments the basket has at least one overflow-relief aperture having a second aperture dimension larger than the at least first aperture dimension; the overflow-relief aperture being positioned adjacent to the top of the manifold body when the manifold body is affixed within the vacuum device. In many other such embodiments the basket has a plurality of apertures of at least two different aperture dimensions, and wherein the apertures disposed proximally along the basket have a larger aperture dimension than the apertures disposed distally along the basket. In still many other such embodiments the basket has at least one protrusion disposed around the circumference thereof configured to cooperatively engage with at least one indentation disposed within an inner wall of the manifold body to affix the basket therein. In yet many other such embodiments the at least one protrusion uniquely orients the basket within the manifold body when coupled with the at least one cooperative indentation.

In still yet other embodiments the proximal end of at least one suction port is configured to mate with a suction tube.

In still yet other embodiments the suction port assembly comprises a plurality of suction ports.

In still yet other embodiments the suction port assembly further comprises a sealing element configured to provide a fluid seal between the suction port assembly and the proximal end of the manifold body. In many such embodiments the sealing element is an O ring.

In still yet other embodiments the suction port assembly further comprises at least one mechanical lock configured to securely interconnect the suction port assembly with the proximal end of the manifold body.

In still yet other embodiments the suction port assembly comprises at least two suction ports, and wherein the at least two suction ports have distal outlets that extend Within the internal volume of the manifold body, and wherein at least one suction port distally extends further within the manifold body than at least one other suction port. In many such embodiments the variation of distal extension of the at least two suction ports are configured to reduce turbulence of a flow of fluid into the internal volume through the suction ports.

In still yet other embodiments the suction port assembly is comprised of four suction ports. In many such embodiments two suction ports are disposed as upper suction ports and two suction ports are disposed as lower suction ports, such that the upper suction ports are positioned above the lower suction ports relative to the direction of gravity when the manifold body is affixed within the vacuum device. In many other such embodiments the distal ends of the upper suction ports are longer than the distal ends of the lower suction ports, and wherein the distance that the distal ends of the lower suction ports extend within the internal volume is configured such that the distal ends are disposed above the lowest portion of an overflow aperture disposed within the filter element, such that reflux of waste up the outlets of the suction port tubes is prevented.

In still yet other embodiments the at least one suction port has a scalloped opening at the distal end.

In still yet other embodiments he manifold further includes at least one cap capable of fitting onto the proximal portion of the at least one suction port. In many such embodiments the manifold includes a tether interconnecting the at least one cap to the suction port assembly. In many other such embodiments the manifold includes at least one support gusset that binds a sidewall of the at least one cap with the tether.

In still yet other embodiments the vacuum port comprises a resilient valve body having an openable orifice disposed therein. In many such embodiments the orifice comprises at least one slit that allows for insertion of the vacuum inlet. In many other such embodiments the valve body comprises at least one wing disposed on the valve body edge and configured to cooperatively engage the distal end of the manifold body. In still many other such embodiments the valve body has a dome-like shape that protrudes into the manifold body. In yet many other such embodiments the valve body is configured such that the vacuum inlet fits within the dome-shaped valve body forming a fluid seal therewith.

In still yet other embodiments the vacuum port is offset from the axial center of the distal end of the manifold body.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying drawings, which are shown in schematic form, wherein:

FIGS. 2A and 2B provide schematic perspective and side see-through views of a waste manifold in accordance with embodiments.

FIGS. 6A and 6B provide schematic cross-sectional views of a waste manifold body in accordance with embodiments.

FIGS. 8A and 8B provide schematic side and front views of a waste manifold filter in accordance with embodiments.

FIG. 11 provides a schematic rear partially-disassembled perspective view of a waste manifold in accordance with embodiments.

FIGS. 12A to 12G provide schematic perspective, side and cross-sectional views of vacuum port seals in accordance with embodiments.

FIGS. 13A to 13F provide schematic cross-section views of vacuum port seals in accordance with embodiments.

FIGS. 17A to 17E provide schematic perspective and partially cross-sectional views of a waste manifold suction port assembly in accordance with embodiments.

DETAILED DESCRIPTION OF THE INVENTION

Figures 1A, 1B:
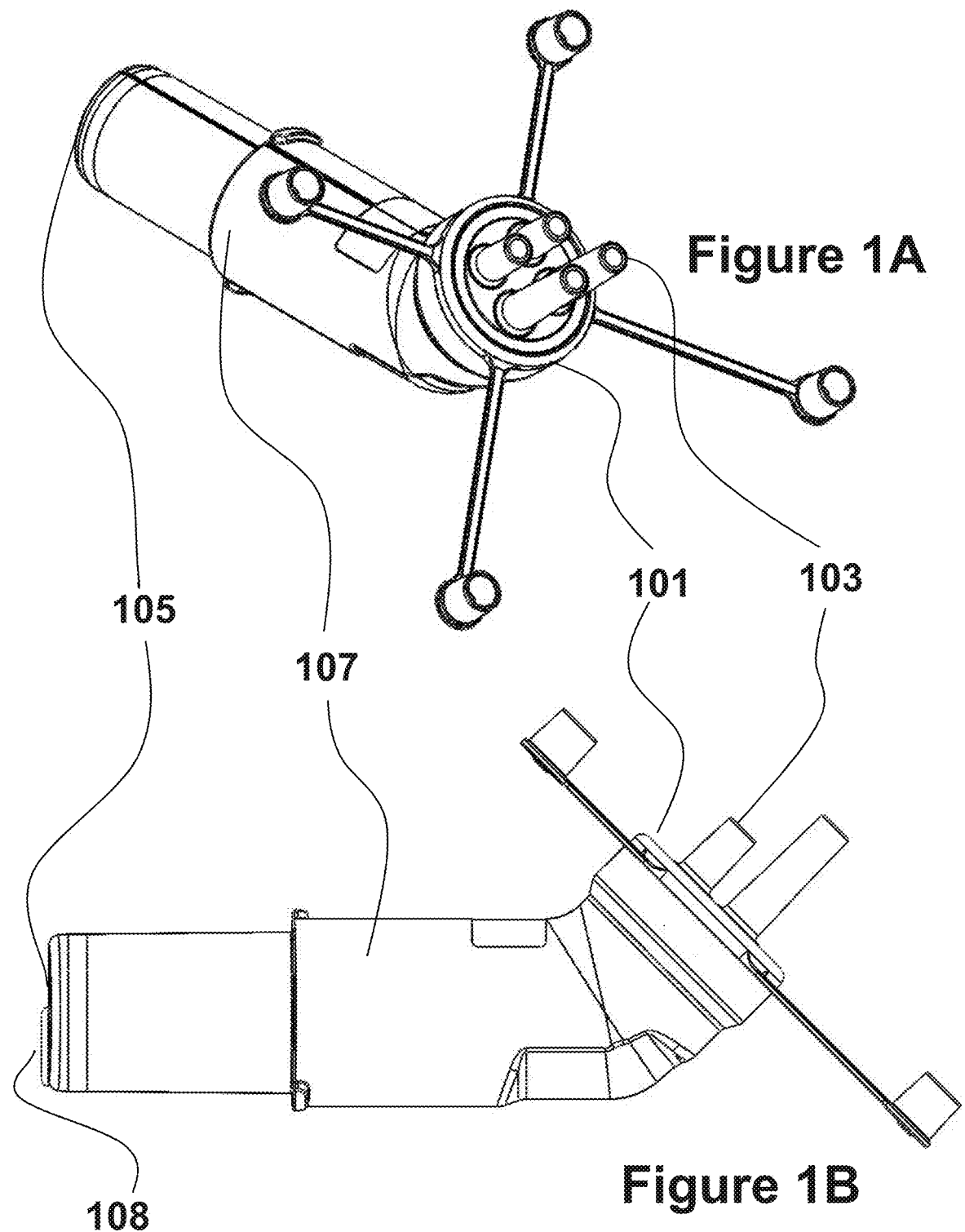
FIGS. 1A and 1B provide schematic perspective and side views of a waste manifold in accordance with embodiments.

Turning to the drawings, medical waste collection manifolds that may connect to a vacuum system to create suction, such that liquid, semi-solid, or solid biological or medical waste may be collected are provided. In many embodiments, the manifold is configured to collect hazardous waste in a manner to ensure proper containment.

In several embodiments, a waste collection manifold has a proximal end with a suction port that could mate with a suction tube that could communicate with the site of waste generation. In several more embodiments, a manifold has a distal end with a vacuum port designed to mate with a different tube that could communicate to a vacuum. In other embodiments, a manifold has a body to connect the suction port and vacuum port. In other more specific embodiments, a manifold body is angled. Some embodiments are directed to filter devices that may trap solid or semi-solid waste. In more particular embodiments, a filter device is a basket. Some other embodiments are directed to a valve body that could be used at a vacuum port. In addition, many embodiments are directed to modular parts capable of forming a waste collection manifold. Likewise, some other embodiments are directed to a method of assembly of a waste collection manifold.

In many embodiments, a manifold body has a tubular shape that extends from the suction port to the vacuum port. In more particular embodiments, a manifold body tube has a circular cross-sectional shape. In other particular embodiments, manifold body tube has an ovular cross-sectional shape. Some embodiments are directed to the manifold body having an internal fluid flow chamber configured to allow a filter basket to be securely situated therein. In some other embodiments, internal shape of the fluid flow chamber within a manifold body is configured to improve vacuum flow. In many such embodiments internal structures are provided to direct and control the fluid flow within the manifold body. In various such embodiments the internal structures may redirect the fluid flow in one or more directions between the suction port and the vacuum port.

Many other embodiments are directed to a filter basket configured to be situated within a manifold body. In more embodiments, a filter basket is provided with a protrusion configured to cooperatively engage a feature within the manifold body to orient the basket in a particular position within the manifold body. In even more embodiments, a filter basket has apertures to allow flow of air or liquid through the basket. In even other embodiments, a filter basket has apertures of various sizes disposed along the length thereof. In some other embodiments, a filter disc can be situated within a manifold body.

In some embodiments, a valve body at the distal end of the manifold is dome-shaped. In other embodiments, a valve body has a slit that may allow vacuum flow and prohibit solid waste. In other embodiments, a valve body has at least one wing on a portion of an edge that could help secure the valve body in a manifold. In various other embodiments the valve body includes a mechanical portion configured to open or close a fluid pathway between the external vacuum source and the internal volume of the manifold body.

In other embodiments, a suction port at the proximal end of the manifold has at least one elongated port tube that extends from manifold to mate with a suction tube. In more embodiments, a suction port has four elongated ports. Some more embodiments are directed to at least one port tube that extends into the vacuum manifold body. In some alternative embodiments, a flapper valve is positioned on the distal end of a port tube. In other alternative bodies, a flapper prevents back-flow of waste. Even other embodiments are directed to an O-ring that can help form a seal at the suction port. Even more embodiments are directed to at least one hook that could secure the connection of a suction port with a manifold body. Still more embodiments are directed to valves configured to open and close fluid pathways between the internal volume of the manifold body and the suction tubes.

In even other embodiments, a suction port tube comprises a cap to close the proximal end thereof. In some other embodiments, the cover is tethered to the manifold. In some more embodiments, the tether has a wide based at the point of connection with the cover that could help prevent the cap from breaking off the tether. Even some more embodiments are directed to a nub that could strengthen the attachment of the cover to the tether.

In even more embodiments, the vacuum body may be assembled with at least one outer casing that can form the outer cover. In some more embodiments, an outer casing could be lined with a tongue that extrudes outward. In some other embodiments, an outer casing could be lined with a groove that intrudes inward. In even some other embodiments, the tongue of an outer casing can integrate into the groove of another outer casing. In even some more embodiments, the tongue of an outer casing and the groove of another outer casing can weld together.

Although a number of medical waste collection manifolds have been developed, these devices may not adequately address several complications that could arise. Previously described manifolds may have problems of leakage. Leakage could occur at the point of waste entry into the manifold or at the point where the vacuum system is connected to the manifold. Alternatively, leakage may occur at sites of manufacture. In addition, the flow of suction could be hampered in previously described manifolds, which could require a hasty exchange of the manifold while in the midst of a medical procedure. These complications could endanger a patient or personnel involved in the medical procedure, such as by release of the medical waste into the environment.

Accordingly, a need exists for an improved biological waste collection system with improved manifestations such that the safety of patients and personnel are better ensured. As such, several embodiments incorporate a medical and/or biological waste collection manifold that may limit the hazards associated with the waste. More embodiments may specifically limit leakage from the waste collection manifold.

Although the figures and following discussion will provide a detailed description of a number of exemplary embodiments of the waste collection manifold, it should be understood that any number of designs can be used to achieve the basic goals of the device. In addition, it should be understood that the figures are merely schematic, and that the relative dimensions of the various elements and their relative spacings are merely exemplary and could be varied by one of ordinary skill in the art while remaining within the bounds of this disclosure.

Various embodiments of the waste collection manifold are shown in FIGS. 1 to 22, all of which provide a device that may incorporate into a manifold that could collect solid or semi-solid waste arising from a medical procedure.

FIGS. 1A and 1B depict embodiments of a manifold for medical waste collection. As shown, in many embodiments the manifold has a proximal end (101) that may receive medical or biological waste via suction tubes that could mate with a suction port assembly (103) disposed thereon. In addition, a manifold may have a distal end (105) having a vacuum port (108) configured to interconnect with a vacuum device when engaged therewith. Between the two ends, a manifold may have an encased body (107) forming a fluid path there between, which encased body may be configured to trap liquid, semi-solid, or solid waste therein. Although certain numbers and configurations of suction ports and vacuum ports are depicted, it should be understood that any number and configuration of such ports may be provided in accordance with embodiments. Likewise, although many embodiments comprise an encased body (107) wherein the distal and proximal ends thereof are disposed along angularly offset axes, as shown in FIG. 1, it should be understood that any number of encased body configuration are contemplated herein.

FIG. 2 depicts a different embodiment of a manifold for medical waste collection in which the body (201) is encased in a transparent material, allowing for the visualization of its inner contents. In such embodiments, a manifold may have a suction port assembly (203) attached to the proximal end (205) thereof, capable of coupling with suction tubes. In addition, a manifold may have a vacuum port (207) disposed within the distal end (209) thereof, capable of connecting to a vacuum. Within a manifold body along the fluid path formed thereby between proximal and distal ends thereof, a filter element (211) may be disposed to capture waste. Again, although certain numbers and configurations of suction ports and vacuum ports are depicted, it should be understood that any number and configuration of such ports may be provided in accordance with embodiments. Similarly, although a single filter element (211) is shown being disposed therein, it should be understood that any number and configuration of filters may be used capable of separated desired products from the waste flowing therethrough. Likewise, although many embodiments comprise an encased body (201) wherein the distal and proximal ends thereof are disposed along angularly offset axes, as shown in FIG. 2, it should be understood that any number of encased body configuration are contemplated herein.

Figure 3:
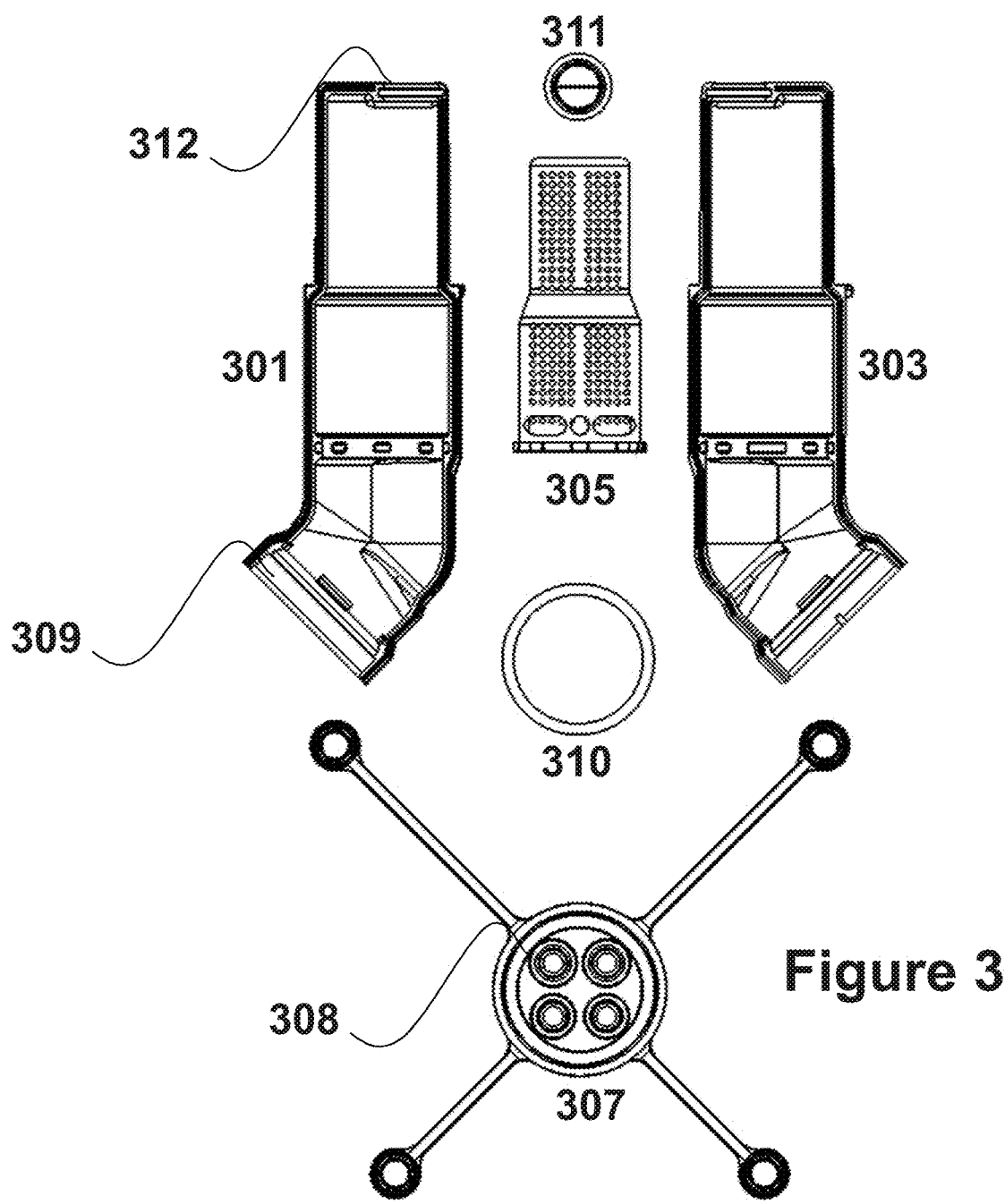
FIG. 3 provides schematic component views of a waste manifold in accordance with embodiments.

An embodiment of an unassembled waste collection manifold in accordance with many embodiments is depicted in FIG. 3. In various embodiments a manifold could comprise a plurality of separate modular parts capable of being assembled together. In accordance with embodiments a manifold could be comprised of a left outer casing (301) and a right outer casing (303) that could be conjoined to form an enclosed body. In addition, a manifold could include a filter element (305) that may be disposed within the enclosed body formed by the left and right outer casings. In such embodiments a suction port assembly (307) comprising one or more suction ports (308) may be attach at the proximal end opening (309) of the assembled enclosed manifold body. In such embodiments a seal (310), such as, for example, an O-ring seal or the like, may be provided between the suction port assembly and the proximal end opening of the assembled manifold body to ensure a fluid tight seal therebetween. Similarly, a valve port (311) may be insert into the distal end opening (312) of a manifold body to form an openable fluid port therein. Again, although certain numbers and configurations of suction ports and vacuum ports are depicted, it should be understood that any number and configuration of such ports may be provided in accordance with embodiments. Similarly, although a single basket filter (205) is shown being disposed therein, it should be understood that any number and configuration of filters may be used capable of separated desired products from the waste flowing therethrough. Likewise, although many embodiments comprise an encased body (formed of casing halves 301 and 303) wherein the distal and proximal ends thereof are disposed along angularly offset axes, as shown in FIG. 3, it should be understood that any number of encased body configuration are contemplated herein.

Figures 4A, 4B:
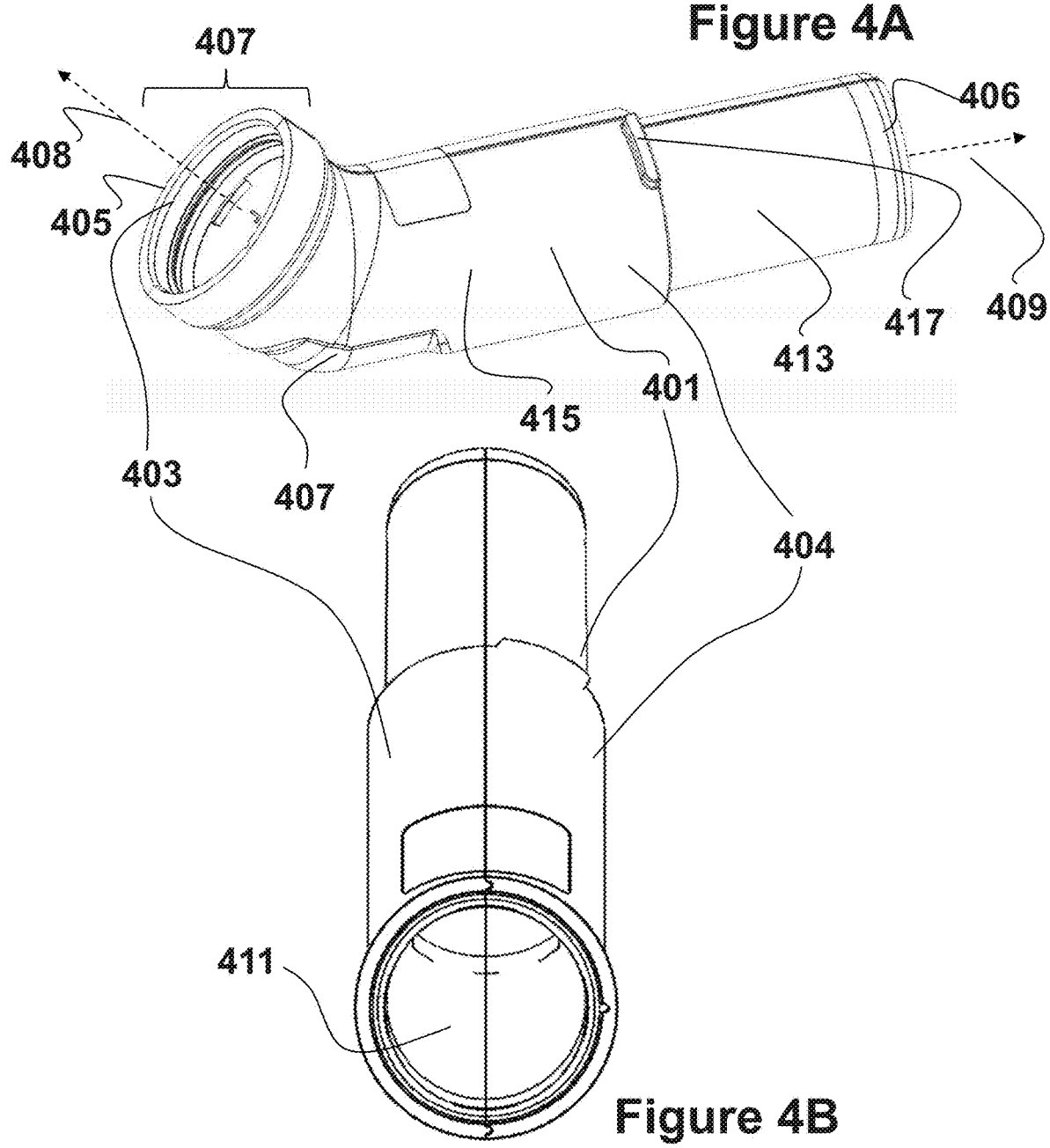
FIGS. 4A to 4C provide schematic perspective views of a waste manifold body in accordance with embodiments.
Figure 4C:
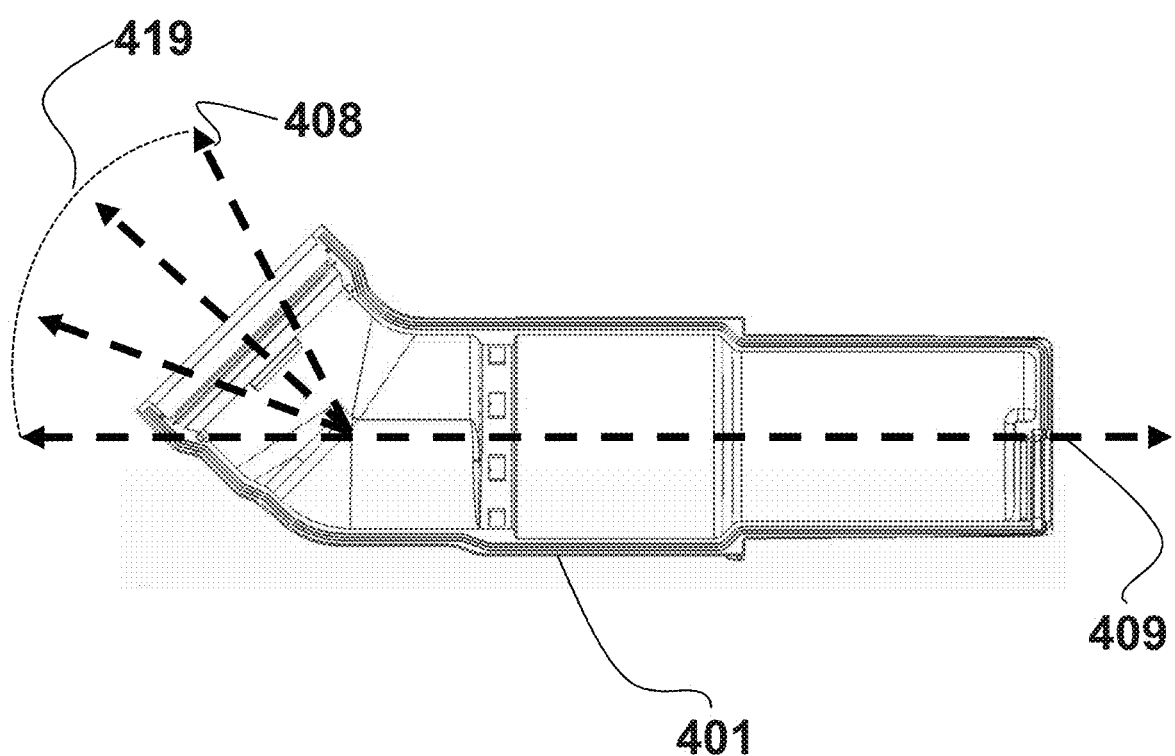

FIGS. 4A to 4C depict an embodiment of an outer casing of the manifold body (401). In many embodiments, when assembled, a left outer casing (403) can mate with a right outer casing (404) to form a body defining an internal volume that is configured to provide an enclosed fluid path between proximal (405) and distal (406) ends thereof. As depicted, a manifold body could be configured such that a least a portion (407) of the body adjacent the proximal end thereof has an axis (408) that is angularly offset from the axis (409) of the distal end of the manifold body, such that, in many embodiments, fluid flow exiting through the vacuum port disposed in the distal end thereof exits along an axis different from the axis through which said fluid entered the manifold body in the proximal end thereof. In some embodiments, a manifold body (401) has a substantially circular cross-section (411). In other embodiments, the distal portion (413) of a manifold body (401) can have a shorter circumference than the proximal portion (415). In some other embodiments, a manifold body may have protrusions (417) that may enable a manifold to engage and lock into a vacuum device (not shown). In such embodiments, the protrusions may be configured such that the manifold may only be oriented in specific configurations with relation to the vacuum device. In many such embodiments the external key features may be configured such that the proximal end axis is angled upward relative to the direction of gravity when the distal end axis is perpendicular to the direction of gravity and the manifold body is in the upright position (e.g., when the manifold is attached to the vacuum device for operation).

As shown in FIG. 4C, the relative angle of axis (408) and axis (409) of the manifold body may be offset (419) from about 25 to less than 90°. Any suitable angle within this range may be utilized so long as axis (408) is offset sufficiently from axis (409) to prevent backflow (i.e., reflux) of biota out of the proximal end of the manifold body. For example, in many embodiments the angular offset (419) is sufficient such that any suction port disposed in the proximal end of the manifold body is positioned sufficiently above the fluid level within the manifold body to prevent backflow of biota out of the manifold body. In addition, in many embodiments the angular offset (419) is sufficiently less than 90° such that the inlet of biota fluid into the manifold body does not impact against the internal wall of the manifold body at an angle normal to the internal wall. Accordingly, in many embodiments the angular offset between the axes is from 25 to less than 90°, in other embodiments the angular offset is from 30 to 60°, and in still other embodiments the angular offset is around 45°.

Figure 5:
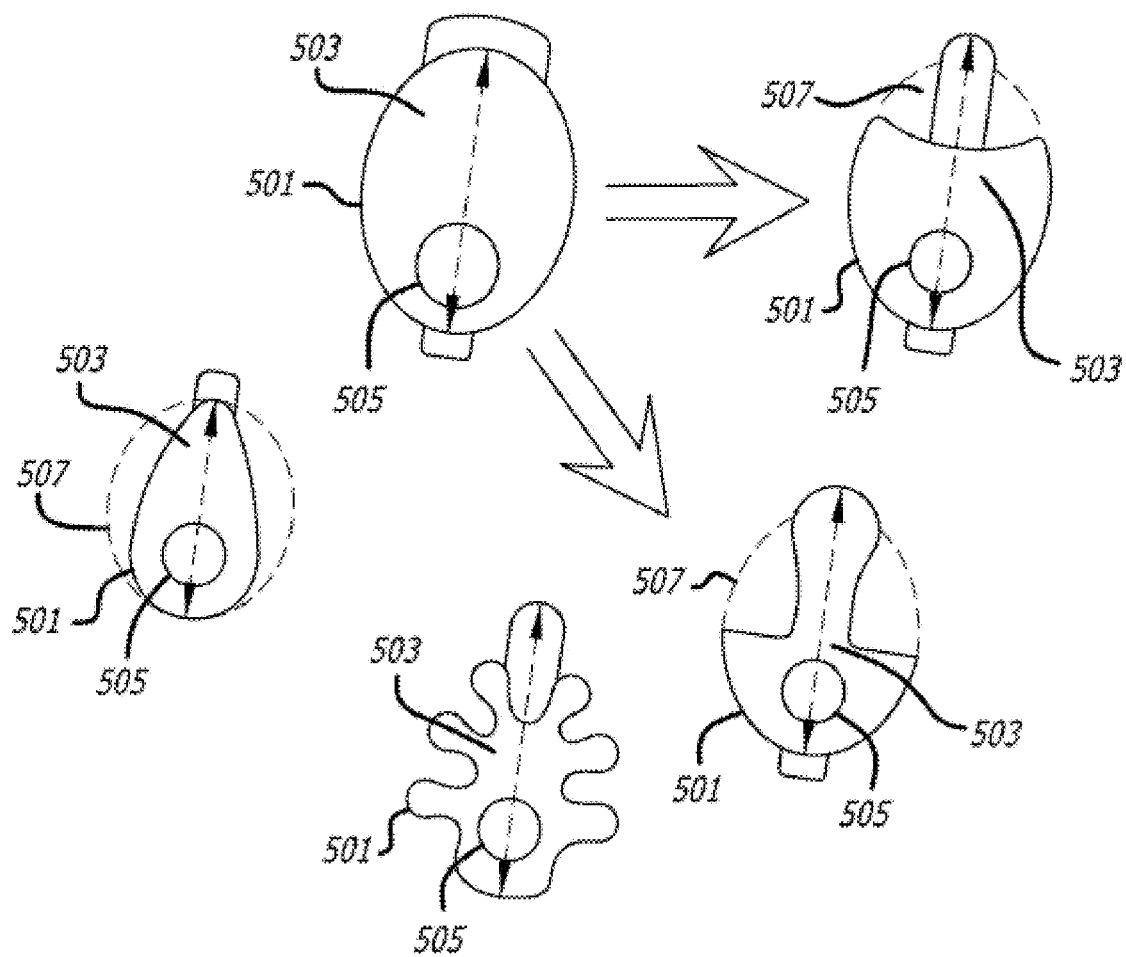
FIG. 5 provides schematic front views of waste manifold cross-sections in accordance with embodiments.

Although a specific configuration of angled ends and variable circumferences are shown, it should be understood that the manifold body may take any number of configurations such that the manifold may be engaged between suction tubes and associated vacuum device. For example, as shown in FIG. 5, in many embodiments a manifold body may have a non-circular cross-section. Indeed, as shown, any arbitrary cross-section may be provided in such manifold bodies so long as the distal end (501) of the manifold body has a cross-sectional dimension (503) sized to cooperatively engage with and rotate in relation to an inlet of the vacuum device such that the vacuum port (505) disposed therein may be interconnected with the vacuum source. Moreover, as shown in the dashed lines (507), in many embodiments the cross-section of the manifold body may change along the length thereof (e.g., increasing or decreasing in size) so long as a sufficient portion of the distal end is dimensioned to allow the vacuum port to cooperatively engage the inlet of the vacuum device. Accordingly, the manifold body can exist in several morphologies along its longitudinal axis, the only requirements of the body being that the vacuum port be configured to cooperatively engage the vacuum inlet (e.g., suction tube) of the vacuum device, that the manifold body have sufficient internal volume to collect solid biota, and that the manifold body be able to incorporate any keyed features that need to interface with the existing vacuum device to ensure a mechanical lock.

FIG. 6 depicts embodiments of outer casing sides configured to cooperatively join to form a manifold body. A first outer casing (601) or a second outer casing (603) can have a proximal end (605) and distal end (607) with a body formation (609) in between. A manifold body in formation (609) can have a bend (611) disposed along the length thereof to alter the angle of the axis between the proximal end (605) and distal end (607) such that fluid traversing the manifold body along the fluid path formed by the formation exits the distal end of the manifold body through the vacuum port outlet (610) along an axis that is angularly rotated relative to the axis of entry to the manifold body defined by the proximal end (605) of the body. As previously described, a filter element (not shown) may be mounted within a manifold body along the fluid path formed thereby. In many embodiments the outer casings may include at least one indentation (613) formed within the inner wall of the cases that would be configured to cooperatively engage mating protrusions disposed within the outer wall of the filter element. In many such embodiments the mating of the indentations and the cooperative protrusions affix the filter element in place when the filter element is disposed between the first and second outer casings are cooperatively joined. As further shown, the size and/or spacing of the indentations may be varied (614) to correspond with similarly varied protrusions disposed in the filter element such that the cooperative engagement of the casing indentations with the filter element protrusions uniquely orient the filter element in relation to the manifold body. In addition, a manifold body formation (609) can have a depression (612) disposed on the lower portion of the casing. A depression (612) in the manifold body can allow for a filter element to situate such that the lip of the basket locates within the depression (613) formation. Furthermore, a depression (612) in the manifold body can also allow for a portion of the inner wall of the filter element to be flush, or near-flush, with the inner wall of the lower portion of the casing such that the flow of waste material therein is not occluded by the lip of the filter element.

Figure 7A:
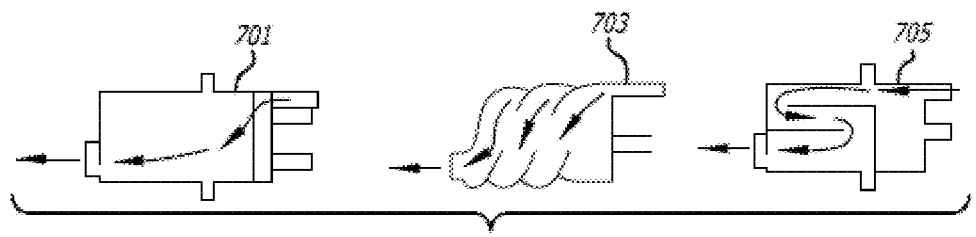
FIGS. 7A to 7C provide schematic cross-sectional views and side views of flow paths within waste manifold bodies in accordance with embodiments.
Figure 7B:
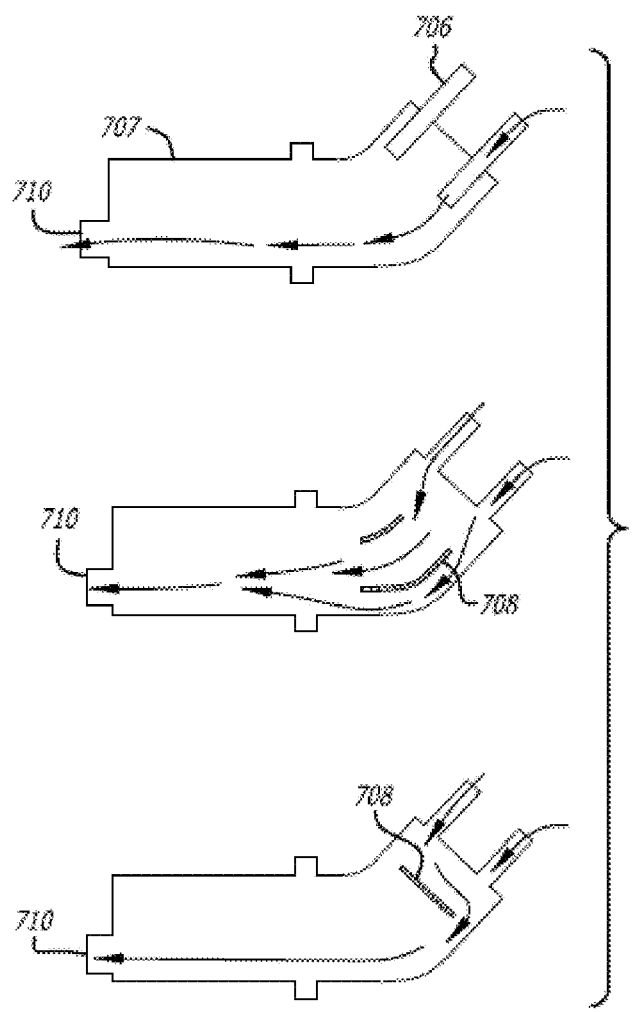

Although many embodiments show a fluid path that flows in a direct line through a manifold body from proximal to distal ends, it should be understood that the internal cavity of the manifold body may be configured or have elements disposed therein to create any desired fluid path. For example, as shown in FIG. 7A, in embodiments the fluid path may be direct (701), or incorporate internal features, such as fins or internal passages to provide any number of non-linear fluid path configurations, including, for example, a helical flow path (703) or a serpentine flow path (705), among others, without altering the fundamental structure of the manifold. Alternatively, in some embodiments, as shown in FIG. 7B, the suction port tubes (706) may be extended into the manifold body (707), or the walls of the manifold body may include flow-directors (708) such as wings, foils, baffles, or channels. These extended suction tubes and/or flow-directors may be configured to redirect the flow to improve flow from the suction port tubes through the manifold body, into the filter, and through the vacuum port (710) out of the manifold body. In other instances, the extended suction tubes and/or flow-directors may be configured to prevent the accumulation of fluid and debris within the manifold body and/or filter by helping to wash the manifold body and filter walls to improve flow. In yet more instances, the extended suction tubes and/or flow directors may be configured to impede flow to intentionally accumulate material in preferential aspects of the manifold body and filter.

Figure 7C:
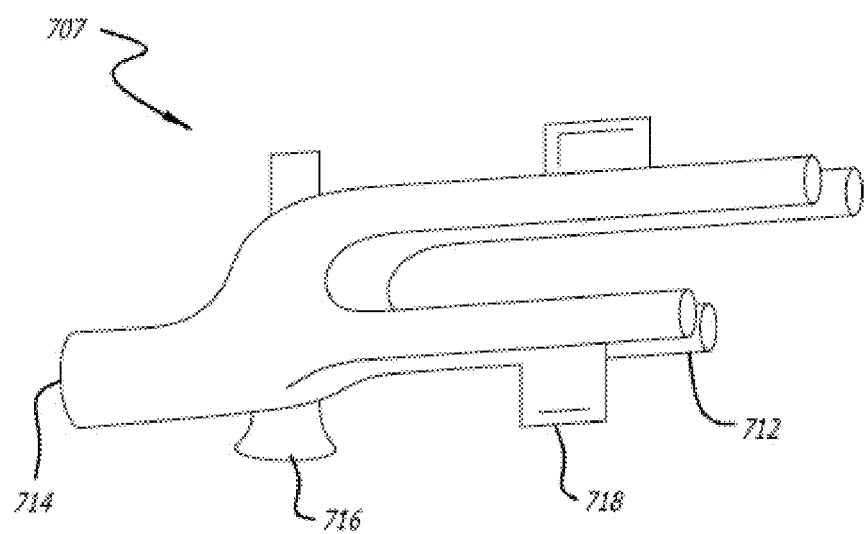

Although the above embodiments all show manifold bodies having proximal and distal inlets and outlets, in fluid communication with each other through a manifold body, it should be understood that any configuration may be provided that allows for biota to flow between a suction port inlet and a vacuum outlet port. As shown in FIG. 7C, many embodiments of manifolds (707) eliminate opposing ends and enables fluid communication between four suction ports (712) and one vacuum port (714). In such embodiments, tabs (716) may be disposed and configured as required to interface with the keyed surfaces of the vacuum device for positive location and appropriate mechanical fixation therewith. In these embodiments there is no "manifold body" as all the suction port tubes and vacuum port mate at desired location along the length thereof. Likewise, there are no ends, only interconnected fluid communication pathways.

Although the embodiment shown contains straight pathways that deviate from their individual axes and merge, it should be understood that the fluid communication pathways could be more complex, convoluted, and/or tortuous. A tortuous pathway could be a preferred embodiment if, for example, the fluid communication pathway is used to mix or homogenize the material passing through the pathway. Similarly, if maximal surface area contact is desired (i.e.,—a catalytic surface), a tortuous pathway could ensure that laminar flow is discouraged to enhance flow within the boundary layer. A spiral flow path could be desirable if a large length to diameter ratio is required to achieve the desired flow profile. It is conceivable that, in such embodiments, the suction and vacuum ports could be connected by a series of valves (not shown) to control flow between the various flow-paths within the manifold. Another embodiment of this exhaust manifold contemplates placing struts or webs of material (718) between the various flow pathways to increase the overall device mechanical strength (e.g.,—add webs of material between suction ports to increase the torsional strength of the device which improves twisting the device to mount it to existing equipment). The webs or struts of material may also be configured to enhance the function of the orienting/seating tabs (716).

FIG. 8 depicts an embodiment having a basket filter element (801) having a plurality of fluid apertures (802) disposed in the walls thereof, the basket filter element being configured to be secured within the assembled manifold body (803). In many such embodiments, the proximal end of a basket can have at least one protrusion (805) near the basket lip (806). The protrusions (805) could be configured to cooperatively engage indentations that may be located within the inner wall of an outer casing (807). As such, each mating protrusion and respective indentation would have a complimentary size such that they could cooperatively couple and secure the basket filter within the manifold body. Some protrusions and their respective coupling indentations may have different sizes such that a basket can only be situated within the body in a limited number of orientations. In one embodiment, a large protrusion (808) and respective coupling indentation are disposed on the basket filet and manifold body, respectively. In another embodiment, a basket filter (801) is configured to be secured and oriented within a manifold body (803) such that an aperture (809) having a larger opening is disposed adjacent to the top portion of the body such that it serves as fluid overflow relief in the event that fluid flow through the other apertures of the basket filter element become occluded.

Figure 9:
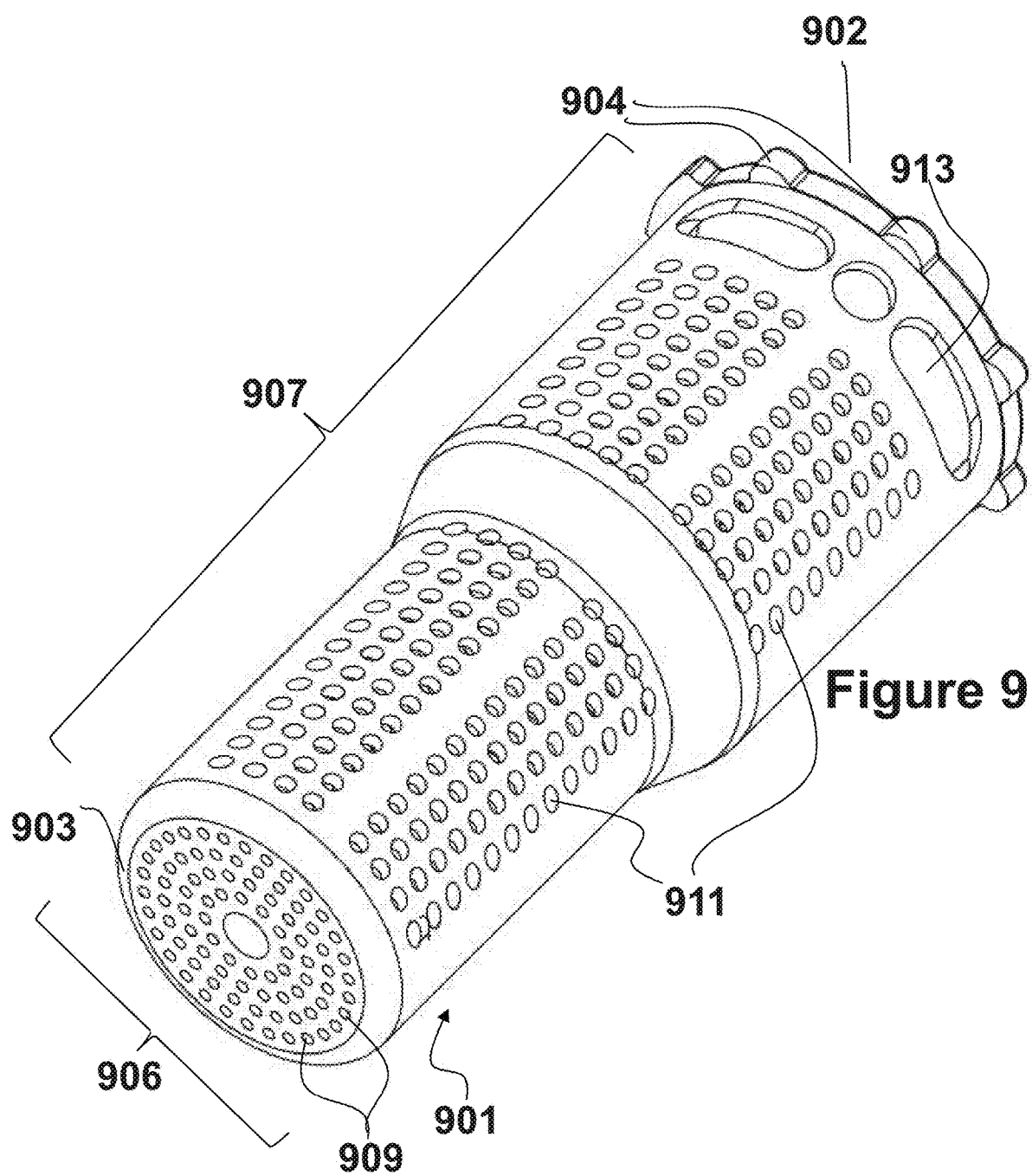
FIG. 9 provides a schematic perspective view of a waste manifold filter in accordance with embodiments.

An embodiment of a basket filter (901) defining and internal volume is depicted in FIG. 9. In many embodiments, a basket filter (901) may include proximal (902) and distal (903) ends configured such that the proximal end has a large fluid opening and at least one protrusion (904) disposed around the circumference thereof and configure to cooperatively couple with indentations on a manifold body to secure the basket filter therein. A basket filter may include a plurality of apertures disposed along the length of the body thereof. In many embodiments the plurality of apertures may be located on the distal wall (906) and/or the sidewall (907) of the basket filter body. In some embodiments, the apertures may be formed with different opening sizes. For example, in many embodiments distal-wall apertures (909) may be formed that have smaller openings than sidewall apertures (911). In other embodiments, the most proximal sidewall aperture(s) (913) may have larger openings than distal sidewall apertures (911). In even other embodiments, when smaller aperture(s) are clogged, larger apertures may allow for continued vacuum flow by providing non-occludable overflow fluid paths. Embodiments of the basket (901) may also have a cross-sectional circumference that varies along the length thereof (e.g., in some embodiments the distal cross-section circumference is shorter than the most-proximal cross-sectional circumference).

Figure 10A:
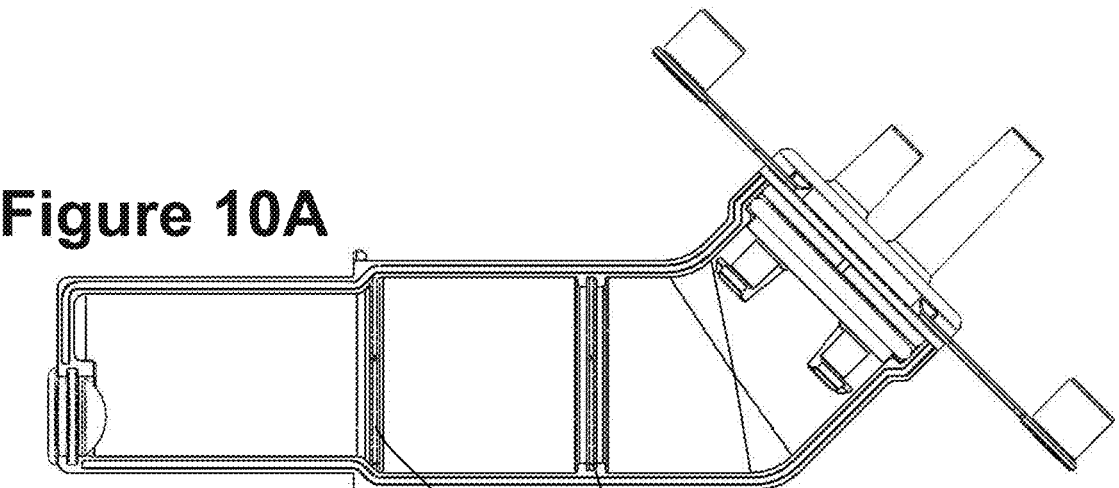
FIGS. 10A and 10B provides schematic cross-sectional and partially disassembled perspective views of a waste manifold filter in accordance with embodiments.
Figure 10B:
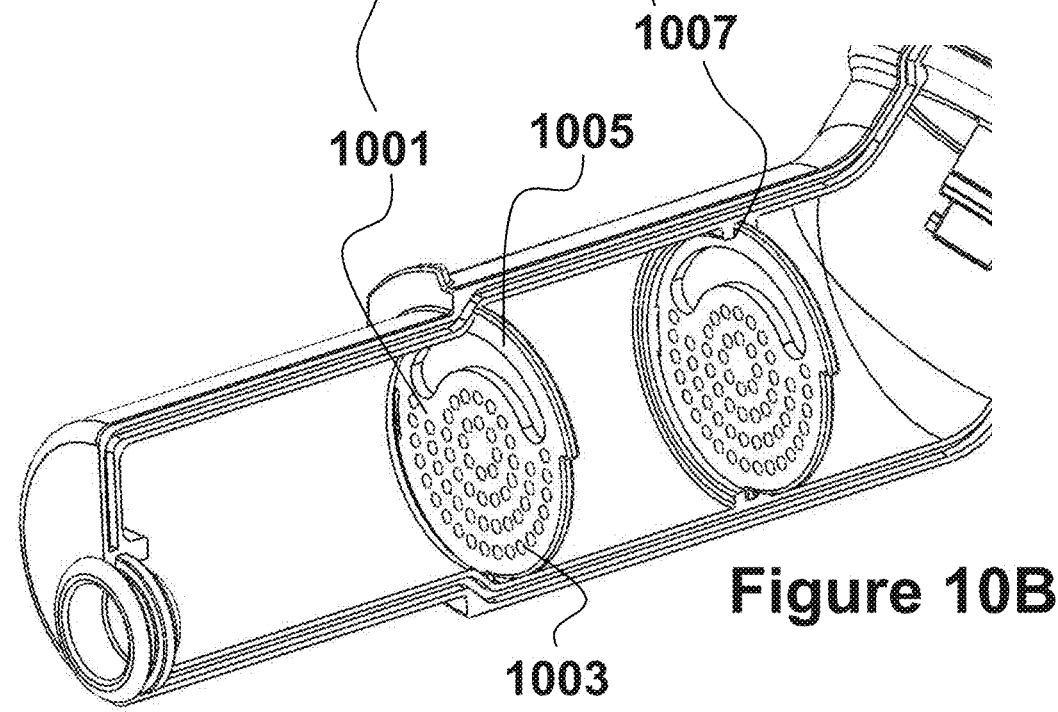

Although basket filter elements have been described thus far, it will be understood that alternative filter element configurations may be incorporated into the manifold design in accordance with embodiments. For example, in various embodiments the basket filter may be replaced by a cone filter (not shown). The use of a cone filter enables off-the-shelf filter material (paper, wire or plastic mesh, porous films, etc.) to be folded into a cone and placed within the manifold body. Such an embodiment requires no tooling and will be easy to re-process and/or change filter design on demand. In still other alternative embodiments, as depicted in FIG. 10, at least one aperture-containing filter disk element (1001) may be used in place of, or in conjunction with, a basket. In many such embodiments, an aperture-containing filter disk element may contain apertures of different sizes. In some embodiments, smaller apertures are located on the lower portion (1003) of a disk and larger apertures are located on the upper portion (1005) of a disk filter (relative to fluid flow). In various such embodiments, larger apertures may allow for continued vacuum flow if smaller apertures become clogged by providing overflow fluid flow. Embodiments are also directed to an aperture-containing disk filter element (1001) that may fit into the manifold via a groove (1007) or cooperative protrusions, such that at least a portion of an edge of a disk filter cooperatively engages the manifold body to secure said disk in relation thereto.

Although specific arrangements of filter elements, apertures and securing elements have been set forth above, it should be understood that many variations may be made to such filter elements without departing from the scope of embodiments. In many embodiments the number, size and disposition of apertures within a filter element may be varied. Likewise, although the filter elements have been shown having protrusions that fit within indentations in the manifold body, it will be understood that the such elements may be disposed in an opposite arrangement such that the protrusions are located on the manifold body and indentations are disposed on the filter element without departing from the scope of embodiments.

FIG. 11 depicts another embodiment in which a valve body (1101) can integrate into a vacuum port outlet (1102) disposed in the distal end of a manifold to provide an openable entry through which a vacuum element (such as a suction tube) from a vacuum device may be engaged. In many embodiments the resilient valve body comprises a membrane (1103) formed of a resilient material configured span the valve port (1101), and which may have an orifice (not shown) disposed therein. The location of a vacuum port (1102) and valve body (1101) may be offset from the axial center (e.g., lower portion (1104)) of the manifold body within a distal wall (1105). In some embodiments, a distal wall (1105) is thick enough (1107) such that a valve body (1101) can firmly integrate within the distal wall. In other embodiments, a valve body (1101) has at least one wing (1109) on its edge configured to cooperatively engage a hollow section of the distal wall (1105) to help securely integrate the valve body. In even other embodiments, a valve body (1101) has a groove (1111) such that a protruded edge of the vacuum port outlet can help securely integrate the valve body.

Although a single resilient valve body configuration is shown in FIG. 11, it should be understood that such a resilient valve body comprising a resilient membrane configured to occlude the vacuum port outlet, might be used in association with the manifold. Exemplary embodiments of resilient valve bodies are depicted in FIGS. 12A to 12G. In some embodiments, a valve body has at least one wing (1201) on a portion of its edge configured to be secured within the distal wall of the manifold body (as described in FIG. 11). In other embodiments, a valve body does not have a wing, but incorporates a circumferential groove (1202) configured to engaged the annular opening of the vacuum port outlet (as described in FIG. 11). A valve body may have a dome-like shape (1203) protruding inward. As such, a vacuum element, such as suction tube or equivalent, may be able to fit within a cavity (1205) within a dome-like shape (1203) to form a tight seal. In embodiments, a valve body may have an orifice (e.g., one or more slits) (1207) that allows for vacuum flow, but prevents solid or semi-solid particulate to pass. It would be understood, that alternative perforations within a valve body could be used that may allow for vacuum flow and prevent solid or semi-solid particulate to pass.

Figure 12F:
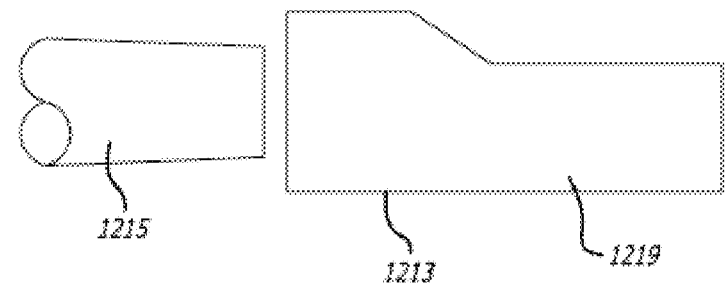
Figure 12G:
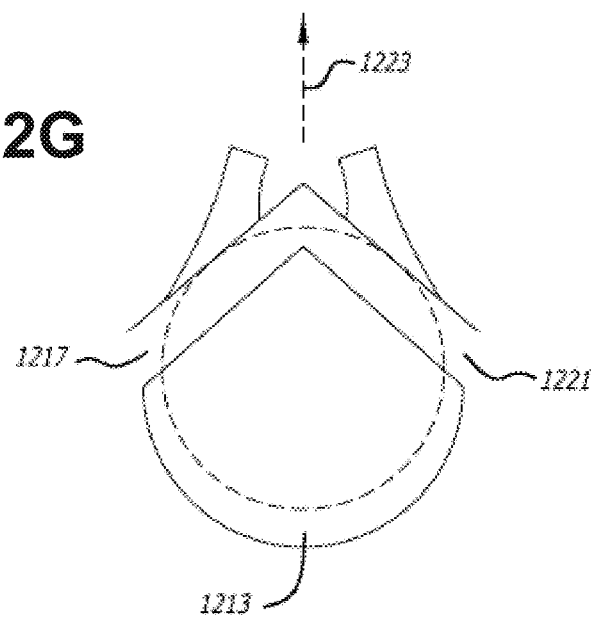

For example, various embodiments, as shown in FIG. 12F may take a duckbill configuration. Regardless of the form taken by such a resilient valve body, the fluid communication pathway at the vacuum outlet port in each case is sealed by a resilient member (e.g., a membrane as shown and described in FIGS. 12A to 12E above, or a barrel resilient valve body (1213) as shown in FIG. 12F). In any of these configuration, as shown in FIG. 12F, upon insertion of the vacuum inlet (1215) into the resilient valve body and progressive insertion into the resilient valve body, the valve body is deformed (as shown in FIG. 12G). This deformation opens a fluid communications pathway (1217) between the vacuum inlet and the interior of the manifold body. For example, in the embodiment shown in FIGS. 12F and 12G a duckbill barrel (1213) with a narrow section (1219) containing a wall with a slit (1221) is provided. In the absence of a vacuum inlet, the wall slit (like a duck bill valve) is closed to prevent fluid communication therethrough. In the presence of a vacuum inlet, the vacuum inlet displaces the wall outward (1223). The mechanism pictured shows the vacuum inlet acting as an internal mandrel to push the walls of the resilient valve body outward thereby opening a fluid communication pathway. Many alternative embodiments using such a barrel configuration may be provided. For example, the barrel may comprise multiple slits along the length of the barrel where insertion of the vacuum inlet compresses the barrel axially causing the walls to buckle outwards thereby opening at least one fluid communicating pathway. In this embodiment, the vacuum inlet does not necessarily insert into the barrel or over the barrel, and the only contacting surface may be the very tip of the vacuum inlet.

Regardless of the specific design of such resilient valve bodies, the natural resiliency of the valve body material closes the fluid communications pathway when the vacuum inlet is removed or no axial load is being applied. For example, a valve body could be alternatively shaped like an umbrella or a needle and still be capable of necessary function. In many such embodiments the resilient valve body may be formed of a resilient polymeric material (e.g., rubber) having a durometer shore hardness value of from 30 to 50 such that the valve body allows for the repeated deformation of the resilient valve body while engaged with the vacuum inlet (such as a suction tube) of the vacuum device while still being sufficiently resilient to maintain a fluid seal once removed from vacuum device. In one embodiment, the resilient valve body could contain a mechanical wiper feature (like an O-ring) that wipes the external surface of the vacuum inlet clean upon removal.

Figure 13A:
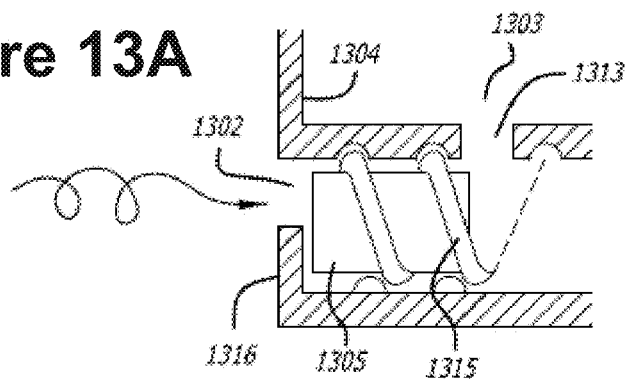
Figure 13B:
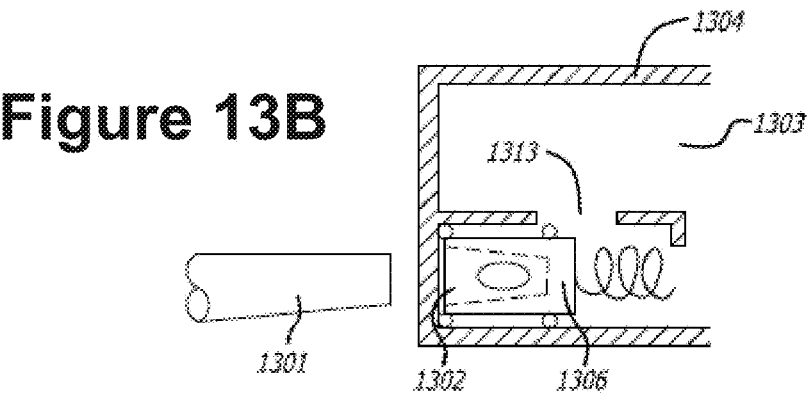
Figure 13C:
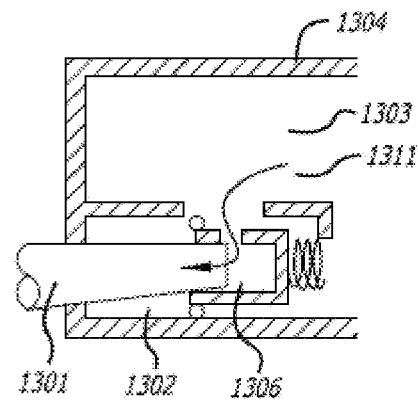
Figure 13F:
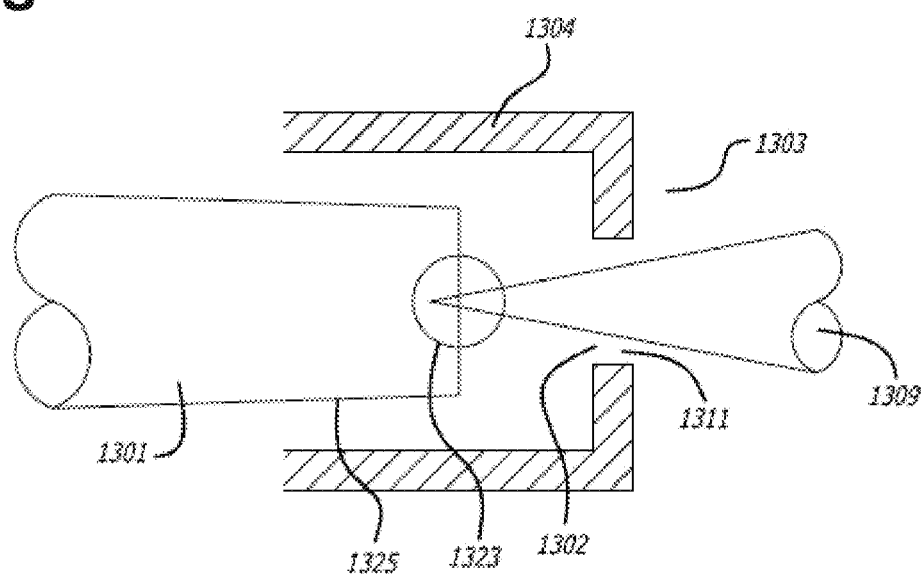
Figure 14:
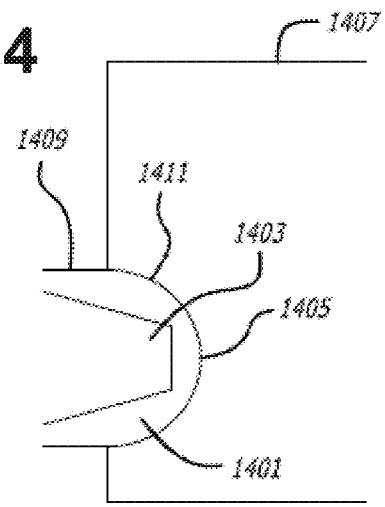
FIG. 14 provides a schematic side views of a vacuum port seal in accordance with embodiments.
Figure 15:
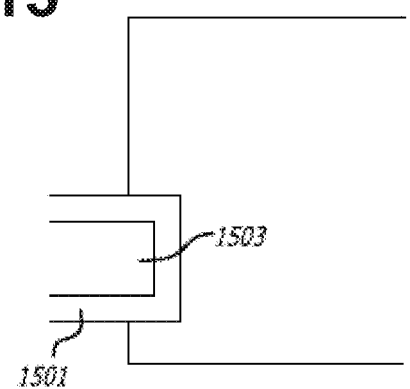
FIG. 15 provides a schematic side views of a vacuum port seal in accordance with embodiments.

Although embodiments of valve bodies incorporating resilient membranes or other mechanisms have been described, it will be understood that valve bodies provided to openably occlude the valve port outlet may be used. FIGS. 13 to 15 provide a number of alternative valve body embodiments. As shown in FIGS. 13A to 13F, in various embodiments a mechanical element configured to move distally when engaged with a vacuum inlet element, such as a suction tube, (1301) of a vacuum device may be used. In such an embodiment the insertion of the vacuum device element (such as a suction tube) into the vacuum port outlet (1302) forces the valve body to move inward thereby opening a fluid path between the interior (1303) of the manifold body (1304). As shown in the Figures, these valve bodies may take a number of forms, including for example, a rotatable element (1305) as shown in FIG. 13A, a spring-loaded element (1306) as shown in FIGS. 13B and 13C, a pivotable element (1307) as shown in FIG. 13D, a receptacle flange (1308) as shown in FIG. 13E, or a needle element (1309) as shown in FIG. 13F.

More specifically, as shown in FIG. 13E many embodiments incorporate a receptacle valve body (1308) that forms a fluid-tight seal with the vacuum port outlet (1302) and interfaces with the inside or outside of the vacuum inlet element of the vacuum device (1301) (e.g., suction tube). In various embodiments a receptacle flange relies on a spring force (not shown) to maintain a closed position before the vacuum inlet is inserted. In the closed position (as shown in the upper portion of FIG. 13E, there is no fluid communication between the inside of the manifold (1303) and the vacuum inlet (1301). Upon insertion of the vacuum inlet, the receptacle flange is displaced inwardly (as shown in the lower portion of FIG. 13E) thereby creating a fluid communication pathway (1311). Although in the embodiment shown, the fluid pathway is formed by a single outlet aperture (1313) that enables fluid communication between the vacuum inlet (1301), the receptacle and valve body (1308), and the interior of the manifold (1303), it should be understood that any number or configuration of such outlet apertures may be contemplated in accordance with embodiments. In various embodiments the outlet aperture could be, for example, a slit, circular hole, or large window that allows controlled flow of material through the valve and into the suction tube. Alternatively, a plurality of outlet apertures could be used to achieve various outcomes like control of flow rates, increase or decrease resistance to flow, or to intentionally clog with debris if particles exceed a predetermined size or shape. The outlet apertures could be used to strain or sieve aspirated materials like a plurality of small circular outlet apertures.

For example, as shown in FIGS. 13A to 13C, a number of different mechanical valve bodies and outlet aperture configurations may be provided. For example, in these embodiments the fluid communication pathway (1311) is perpendicular to the axis of the valve body mechanism. In these sliding configurations, the natural state of the sliding element of the valve body (1305) and (1306) is to prevent a fluid communication pathway from the interior (1303) of the manifold to the vacuum inlet (1301) (see FIGS. 13A and 13B). Insertion of the vacuum inlet (e.g., suction tube) forces a valve body to slide away from its closed position and expose a fluid communication pathway (1311) through a lateral outlet aperture (1313) (as shown in FIG. 13C). The sliding motion may be further accommodated by a rotating motion, such as, for example, from a gentle thread or lead-screw (1315) as shown in FIG. 13A.

Moreover, as shown in FIG. 13A, in such embodiments the vacuum outlet may be raised above the lower wall (1316) of the manifold body (1304). In such embodiments, the position of the valve body in relation to the manifold body would prevent backflow conditions in an open but unpowered state by raising the vacuum port outlet (1302) to the vacuum inlet (e.g., suction tube) relative to the bottom of the manifold body as defined by gravity when the system is in the open position. This may be beneficial for an open valve in the unpowered state (i.e., where no active suction was being applied through the vacuum inlet) as the manifold body would be prevented from draining into the unpowered vacuum inlet prior to application of a suction force.

Alternatively, instead of a sliding component, as shown in FIG. 13D, the valve body may take the form of a hinged component (1307), with one portion (1317) being configured (such as in a spherical form) to seal against the inner wall (1319) of the manifold to reduce leaking of biota from the manifold, and another portion (1321) being mounted to the manifold body (1304). In such embodiments, upon insertion of the vacuum inlet (1301), which pushes the sealing portion of the hinged valve body component (1307) away from the inner wall of the manifold body, the hinge pivots or flexes (as shown in the lower portion of FIG. 13D), thus allowing the sealing component to move and allow biota to be passed through the vacuum inlet. Likewise, when the vacuum inlet is removed, the hinged component closes back to its original position thus closing off the vacuum port outlet (1302) to the vacuum inlet.

In still other embodiments, the fluid communication pathway (1311) from the vacuum inlet (1301) to the vacuum port outlet (1302) is controlled by a needle valve body element (1309) where a tapered surface (the needle element) is seated against the opening of the vacuum port outlet to prevent fluid flow from the interior of the manifold body (1303). Displacement (e.g., axial or rotational) of the tapered surface (1309) gradually opens a fluid communication pathway (1311) between the tapered surface (1309) and the outlet (1302). In one embodiment, the tapered surface (1309) terminates with a flange (1323) of material at its distal end. This flange is configured to engage with the tip (1325) of the vacuum inlet in such a way that insertion of the vacuum inlet causes displacement of the flange and attached tapered surface to create an opening between the valve body and the surface of the vacuum port outlet. Removal of the vacuum inlet enables the tapered surface to re-seat against the outlet opening. In many such embodiments the amount of taper of the valve body (1309) may be controlled to determine the amount of displacement required to provide a fluid pathway between the manifold body and vacuum inlet. In many embodiments, the tapered surface is a cone and the opening is circular. As in many pervious embodiments, a spring attached to the tapered valve body may be provided to ensure the natural state of the needle valve body is to be seated within the vacuum port outlet. In such embodiments, insertion of the vacuum inlet overcomes the spring resistance to open the valve body and create a fluid communications pathway through the entire device (e.g., from the suction port, through the manifold body, through the needle valve body, and out through the vacuum inlet).

Regardless of the specific design of such a mechanical valve body, it will also be understood that in many embodiments the removal of the vacuum inlet (1301) therefrom results in the closure of the fluid pathway. For example, as described many embodiments incorporate a spring element, in such embodiments, on removal of the tube, the spring force presses the valve body to re-seat on the vacuum port outlet thereby reforming a fluid-tight seal. The valve body and/or vacuum port outlet may contain a sharp cutting edge that enhances valve seating and/or enables cutting of tissue fragments that prevent the valve from closing completely. The valve spring strength may be selected to enable valve closing despite accumulated debris from the tissue/fluid aspiration through the vacuum port outlet. Alternatively, the spring strength may be chosen to prevent the valve from crushing tissue contained within an outlet aperture thereby preserving this tissue for later use. A further alternative embodiment contemplates a one-way valve that maintains a closed system prior to application of the vacuum inlet, but that prevents the valve from re-closing after the vacuum inlet (e.g., suction tube) is removed (i.e.,—the valve body does not re-seat after one use). Another embodiment contemplates that the valve bodies may be supplied in an open condition and that irreversibly seat to form a fluid-tight seal after a single use to prevent reprocessing of the manifold.

Regardless of the specific design of the valve body and its mode of operation, as shown in FIGS. 14 and 15, in all embodiments a seating portion (1401) must be provided such that the vacuum inlet (1403) is aligned with the valve body (1405) housed within the manifold body (1407). This seating portion can be of various forms and functions. The purpose of such a seating portion is to maintain contact between the valve body and vacuum inlet as the vacuum device removes biota through the manifold body. The valve can maintain a point contact, tapered (as shown in FIG. 14) and/or a line to line contact, non-tapered (as shown in FIG. 15), with the vacuum inlet. The tapered design (as shown) creates a seating portion (1401) around the vacuum inlet (1403) of a specific diameter towards the distal end (1409) of the manifold body (1407) but reduces it's specified diameter as it moves towards the proximal end (1411) of the manifold body. The non-tapered design maintains the specified diameter of its seating portion (1501) throughout the length of the seating portion contacting the vacuum inlet (1503).

Regardless of the specific design of the seating portion, embodiments may be provided where the valve body interfaces with the inside of the vacuum inlet ensuring that the outside of the suction tube is never exposed to human waste, thereby alleviating the concern where a contaminated vacuum inlet surface interfaces with tissues being collected for future processing or re-implantation (e.g.,—if bone fragment tissues accumulated in the manifold body are to be used in a subsequent bone graft procedure, contamination from the unclean/non-sterile vacuum inlet is a route for communication of disease).

Figure 16A:
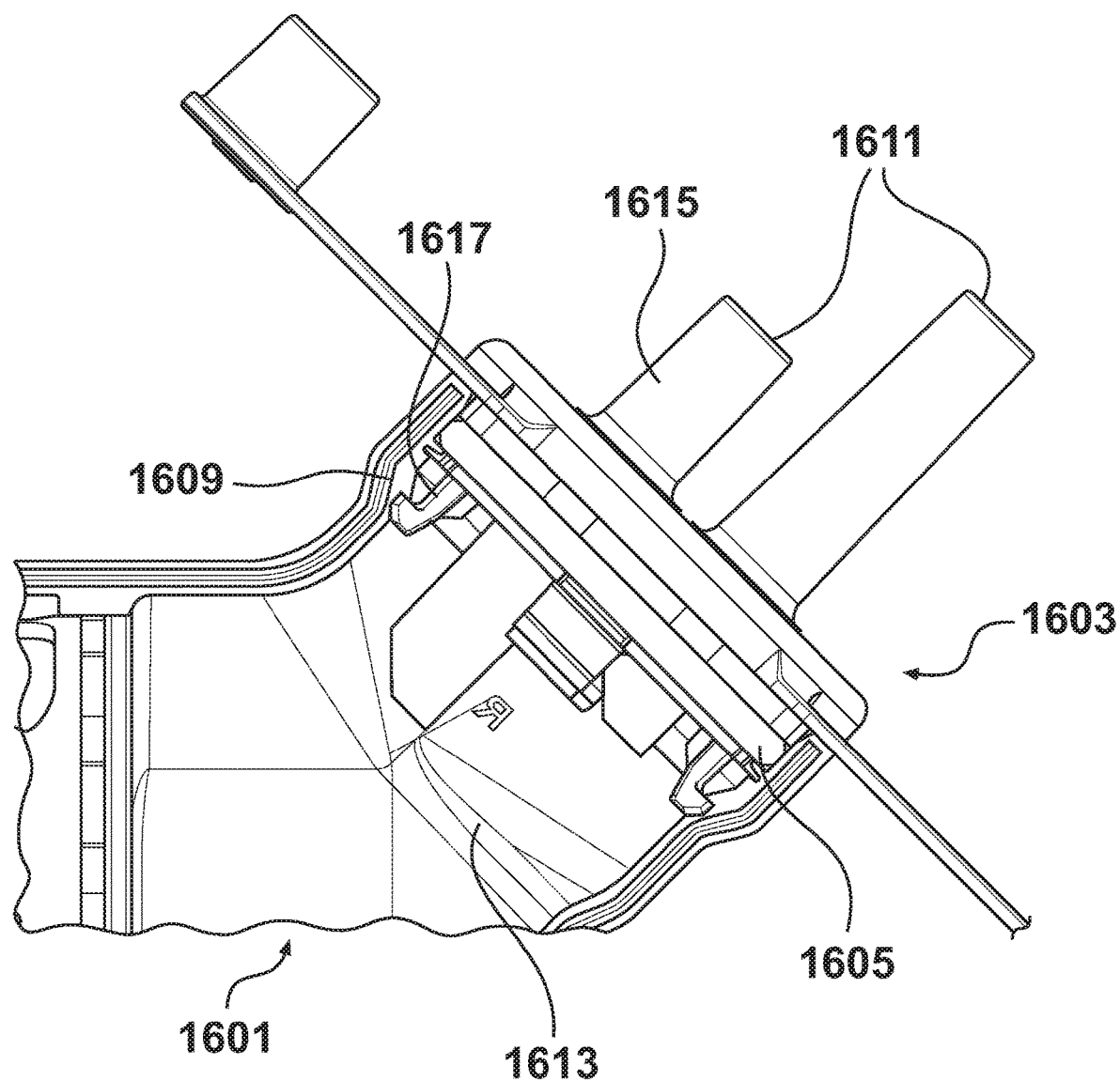
FIG. 16A to 16C provide schematic partially cross-sectional views of a waste manifold suction port assembly in accordance with embodiments.

FIG. 16A depicts an embodiment of the proximal end of a waste collection manifold (1601) that may include a suction port assembly (1603). In some embodiments, a suction port assembly (1603) can attach to the proximal end of a manifold (1601) and be fluidly sealed therewith. Embodiments of a suction port assembly (1603) may have at least one suction port (1611) that provides a fluid pathway through the body of the suction port assembly from outside the waste collection manifold body to inside (1613) the proximal end thereof. Embodiments of a suction port (1611) have at least a portion (1615) configured to mate with a patient suction tube (not shown) that would be inserted as appropriate within a patient to collect biota. Although a specific arrangement of suction ports has been shown, it should be understood that any number and arrangement of suction ports may be incorporated into the suction port assembly as necessary to allow for biota to flow from a patient into the manifold body.

Figure 16B:
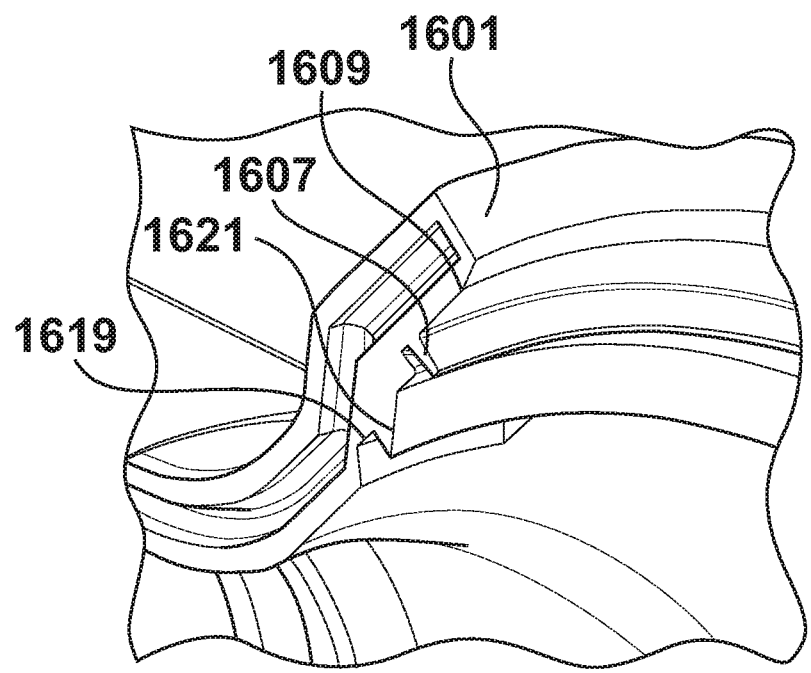
Figure 16C:
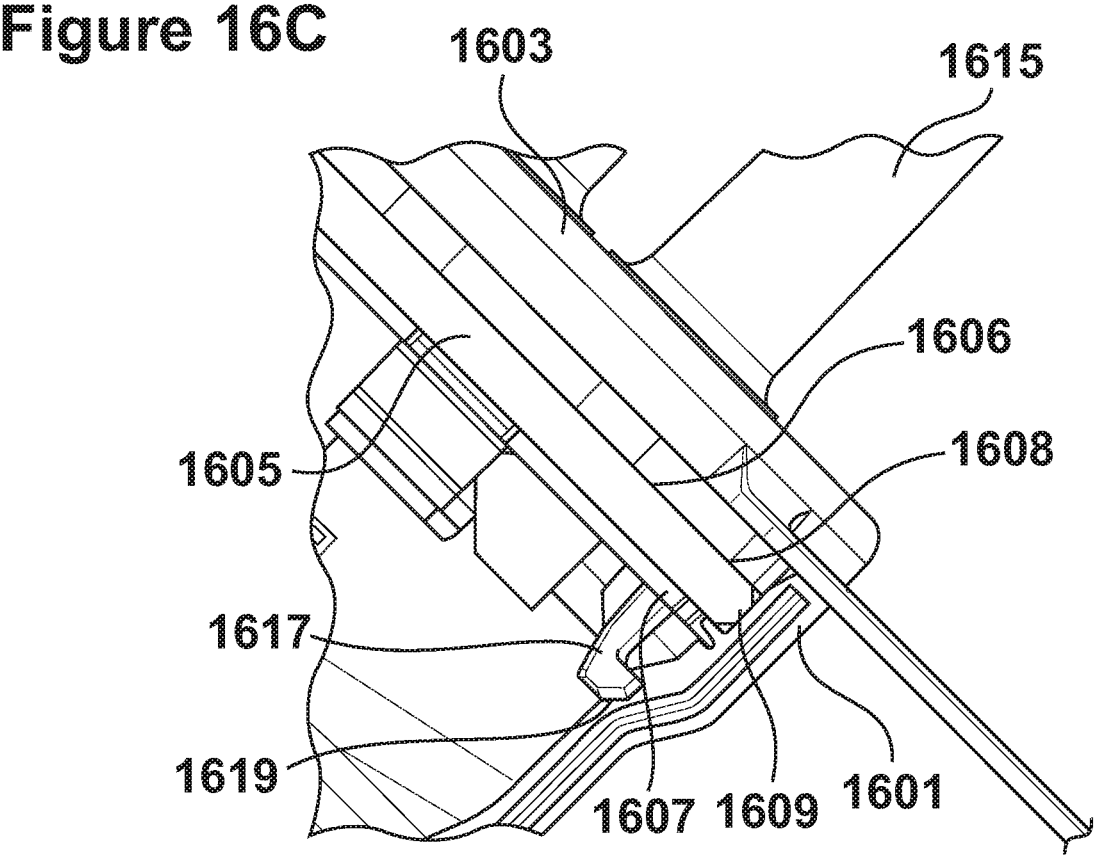

Although the suction port assembly may be integrally formed with the manifold body, in many embodiments, as shown in FIGS. 16A to 16C, a suction port assembly (1603) may be provided that is a separate element from the manifold body (1601). In such embodiments the suction port assembly may incorporate a sealing element (1605), such as, for example, an O-ring seal, capable of forming a fluid tight seal between the suction port assembly and the proximal end of a manifold body (1601). In various embodiments, as shown in detail in FIGS. 16B and 16C, the sealing element (1605) is held between upper (1606), lower (1607), inner (1608) and outer (1609) surfaces disposed between the manifold body (1601) and suction port assembly (1603) such that the sealing element (e.g., O-ring, among other) (1605) is securely held in a sealing arrangement there between. In some such embodiments, a suction port assembly (1603) may also incorporate at least one mechanical lock (1617) (e.g., a latch, press-fit, etc.) to securely interconnect the suction port assembly with a waste collection manifold body (1601). In other such embodiments, the internal surface of the proximal end of a manifold (1601) may include features, such as, for example, grooved intrusions (1609) to cooperatively interact with the mechanical lock (1607) to allow it to engage the waste collection manifold body. In some such embodiments the groove intrusions (1619) comprise an angled element (1621) that encourages the inward movement of the mechanical lock during insertion of the suction port assembly into the waste manifold. The lock mechanism, in accordance with embodiments, may be unidirectional, such that once engaged with the manifold body the suction port assembly cannot be removed from the manifold body.

Figure 17B:
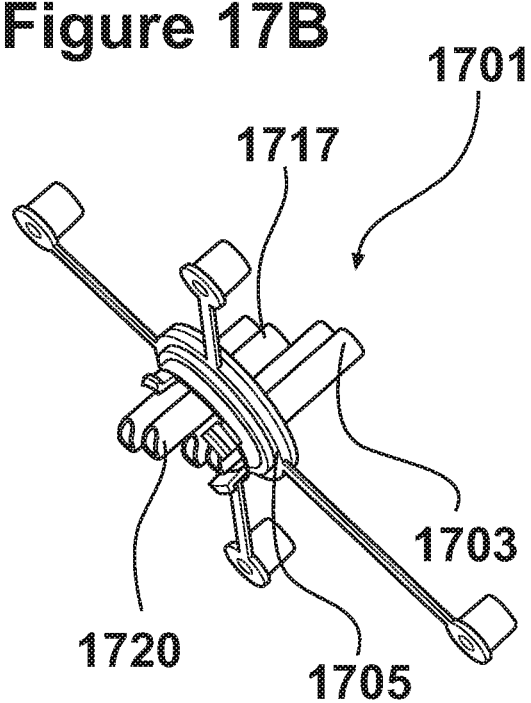
Figure 17C:
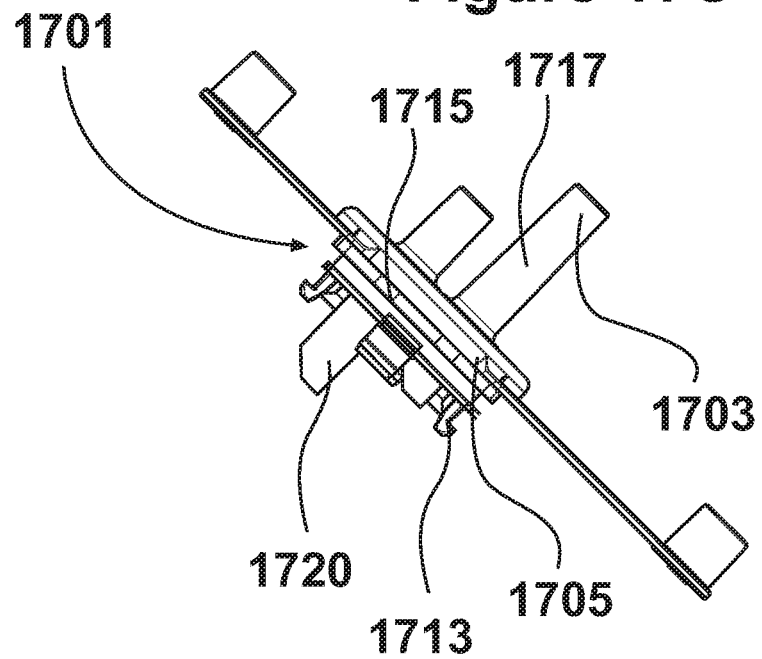
Figure 17D:
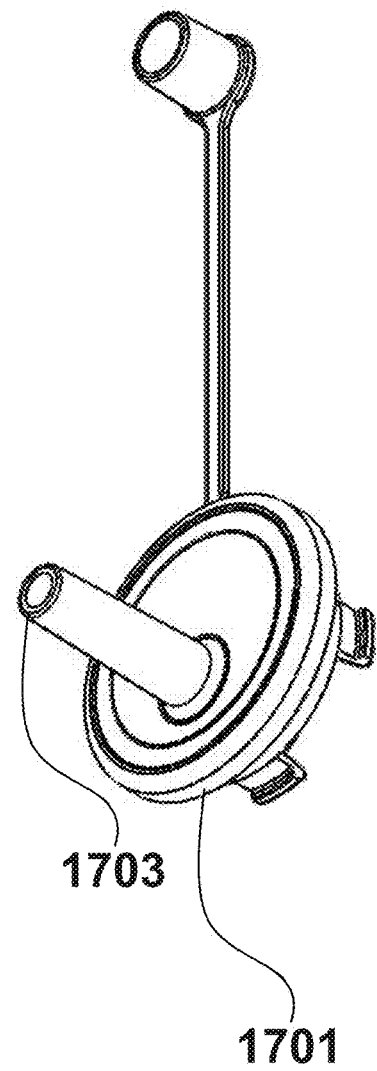

Suction port assemblies in accordance with certain embodiments are depicted in FIGS. 17A to 17E. As shown, in many embodiments a suction port assembly (1701) will have at least one suction port tube (1703) and may have four, or more, suction ports. The number of suction ports may vary depending on application and necessity, for example, an embodiment showing a suction port assembly comprising a single suction port tube is shown in FIG. 17D. In many embodiments, a suction port assembly (1701) will have a body portion (1705) configured to span the opening of the waste manifold to form the proximal wall of a manifold body. In some embodiments, a suction port tube (1703) may begin on a proximal side (1707) of the suction port assembly body (1705) that, when assembled with the waste manifold, is disposed exterior to the waste manifold, and extends through the suction port assembly body into the distal side (1709), that when assembled with the waste manifold, is disposed interior to the waste manifold. Embodiments of a suction port assembly (1703) may have mechanical locking mechanisms, such as, for example, hooks (1713) that may help secure the suction port assembly to the waste manifold. Other embodiments of a suction port assembly (1703) may incorporate a fluid sealing mechanism such as a groove (1715) into which an O-ring can be situated to provide a fluid tight seal between the suction port assembly and the waste manifold.

The proximal portion (1717) of a suction port (1703) may be configured to interconnect with a patient suction tube. In some embodiments, a suction port (1703) will have at least one cap (1718) capable of fitting onto a portion of the proximal portion of a suction port tube (1703). In some particular embodiments, a tether (1719) is attached between a cap (1718) and a suction port assembly (1701).

Figure 17E:
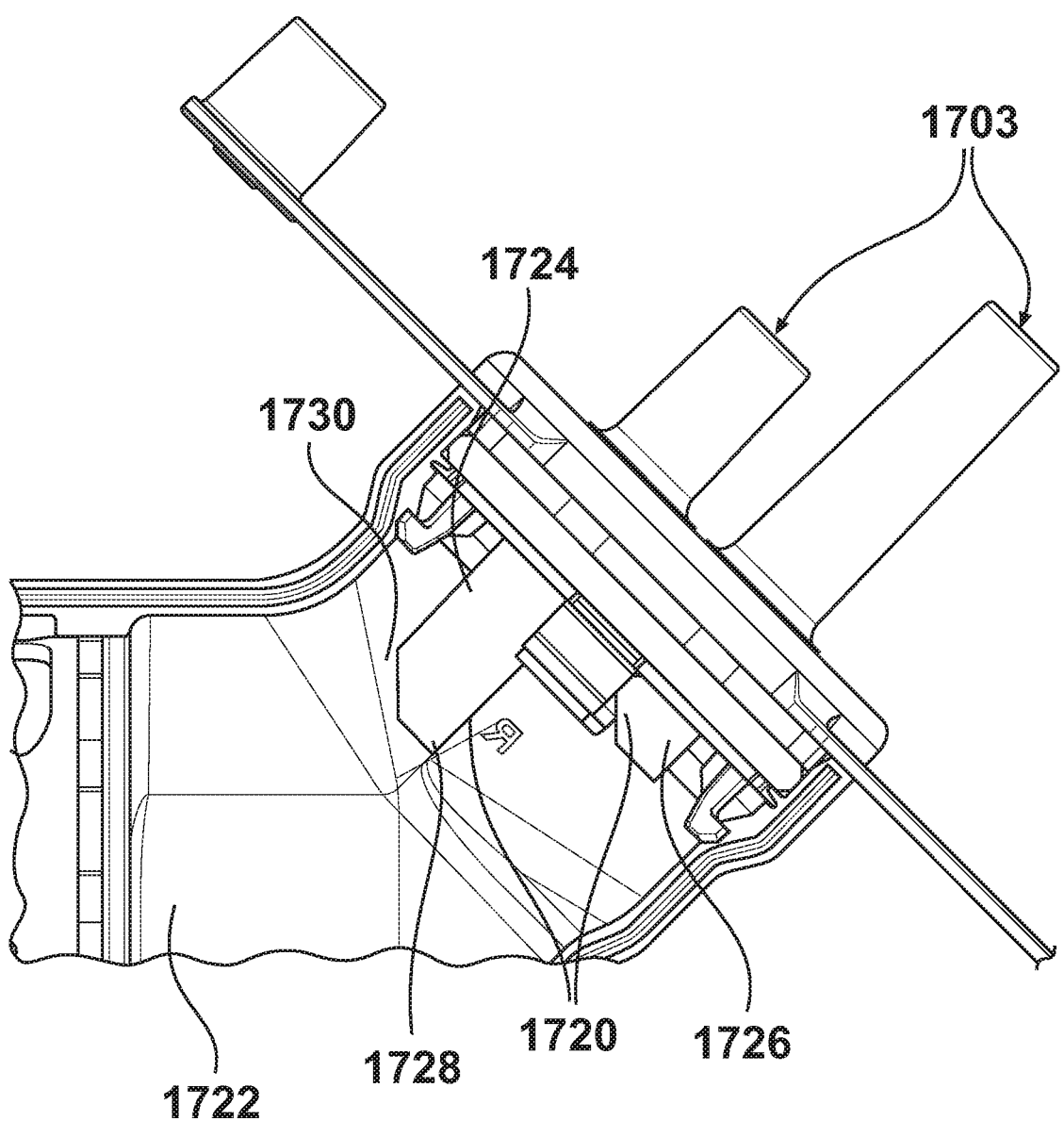

The distal portion (1720) of a suction port tube (1703) may have a variety of lengths and configurations. In some embodiments, as shown in FIGS. 17A to 17C, the suction ports tube may extend into the interior of the manifold body to direct flow. The internally-extended suction port tubes may be configured to optimize flow or prevent accumulated debris from blocking flow. The internally-extended suction port tubes can also enable the collection of particulates in one region of the basket filter to preserve filtration of fluids in other regions of the filter using other ports. In some embodiments, as shown in FIGS. 17A to 17E the extent to which the distal ends (1720) of the suction port tubes (1703) extend within the manifold body (1722) may vary such that the inflow of biota from a patient does not occur at the same point within the manifold body, thus reducing turbulent flow. In some such embodiments, as is shown in FIG. 17E, the length of the distal ends of the suction port tubes may depend on their position relative to manifold body when the manifold body is disposed within and oriented relative to the cooperative vacuum device. In particular, in many embodiments the suction ports may be grouped between upper suction ports (1724) and lower suction ports (1726), wherein the upper suction ports are positioned above the lower suction ports (relative to the direction of gravity) when the manifold body is in the upright position (e.g., when the manifold is attached to the vacuum device for operation). In such embodiments the distal ends of the upper suction ports are longer than the distal ends of the lower suction ports, wherein the length of the distal ends of the lower suction ports are configured such that the outlet of such ports (1728) into the manifold body are disposed above the fluid level within the manifold body such that backflow of biota up the outlets of the suction ports is prevented. Regardless of the specific design and configuration of the suction ports, in many embodiments the distal ends of the suction port tubes are configured to have a scalloped opening (1730), where such scalloped openings may enhance fluid flow and may prevent turbulence within the manifold body.

Figure 18A:
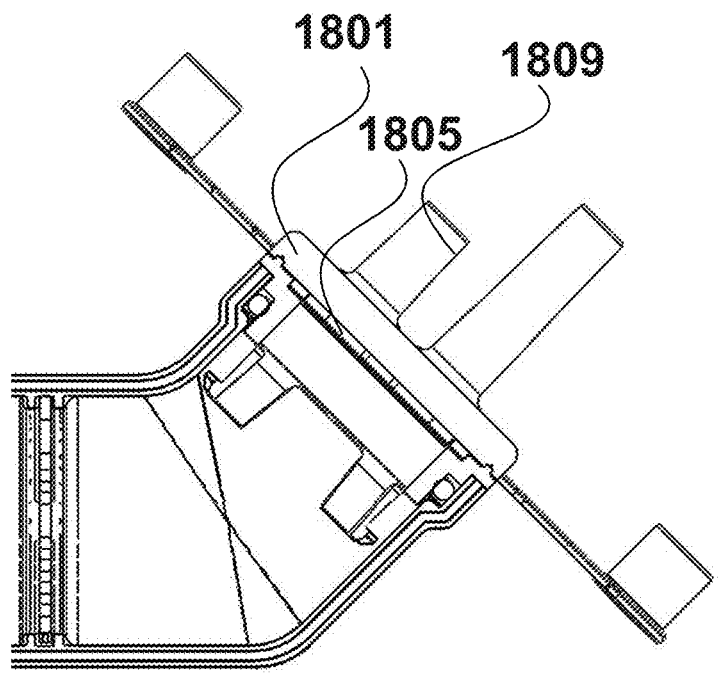
FIGS. 18A to 18D provide schematic partially cross-sectional views of a waste manifold suction port assembly in accordance with embodiments.
Figure 18B:
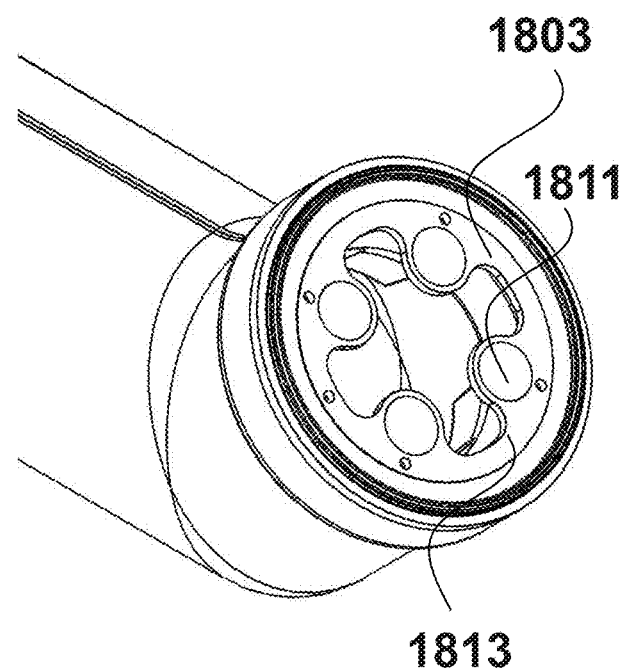
Figure 18C:
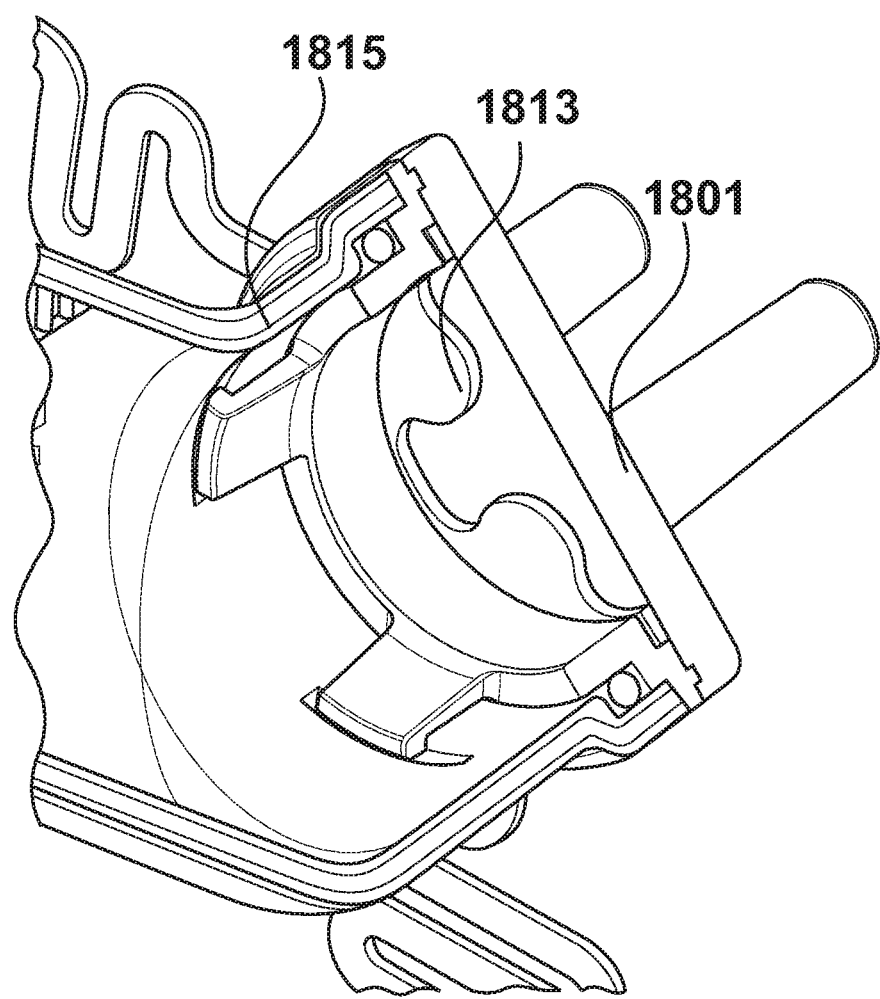
Figure 18C:
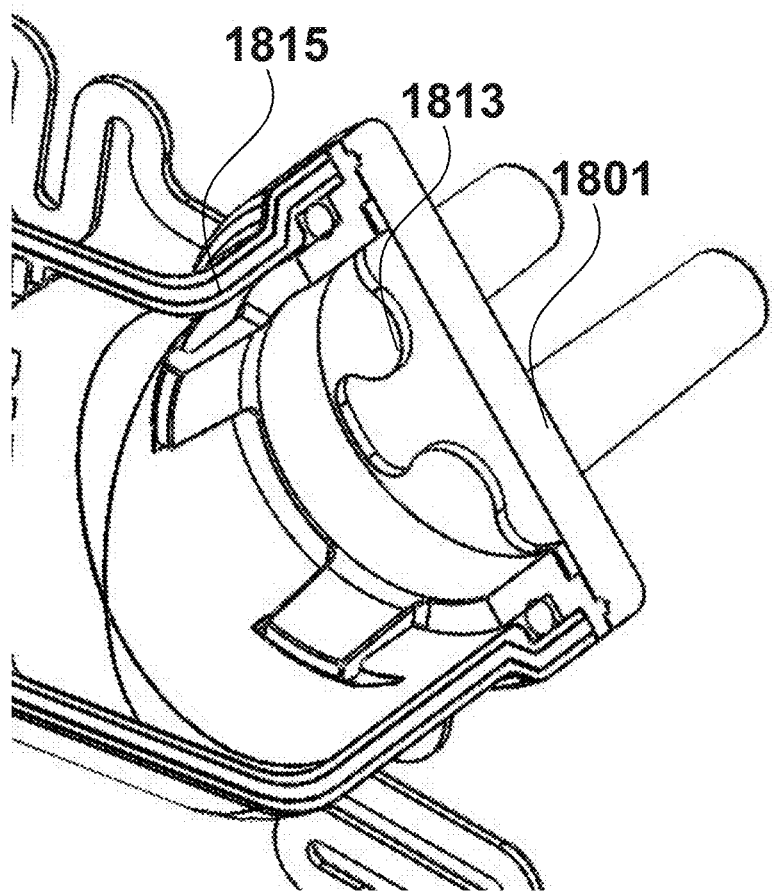

In alternative embodiments, as shown in FIGS. 18A to 18D, a suction port assembly (1801) may incorporate one or more reflux valves (1803) disposed adjacent to the outlets (1805) at the distal end of the at least one suction port tube (1809). As shown, a reflux valve (1803) may take any suitable form (such as for example, a resilient flapper valve or mechanical device) that incorporates a sealing portion (1811) configured to seal the distal end outlet of the suction port tube. A seal between a reflux valve and suction port tube may be configured to prevent backflow of waste or particulate matter back through the suction port tube. In particular, in many embodiments the reflux valve is pre-disposed to maintain a seal with the suction port tube to eliminate biota entering or exiting the manifold body in a static state. In some embodiments, a reflux valve (1803) may be made of a flexible material (e.g., rubber or silicone) that allows it to bend backward when biota is urged through the manifold by the operation of suction from the vacuum device. It should be understood that the specific design of such reflux valves may take many suitable forms and configurations. In many embodiments, as shown in FIGS. 18B and 18C, the sealing portions (1811) of the reflux valve (1803) may be interconnected through an outer ring (1813) that engages within the suction port assembly or between the suction port assembly and manifold body (e.g., at the interface between the manifold body (1815) and suction port assembly (1801)).

Figure 18D:
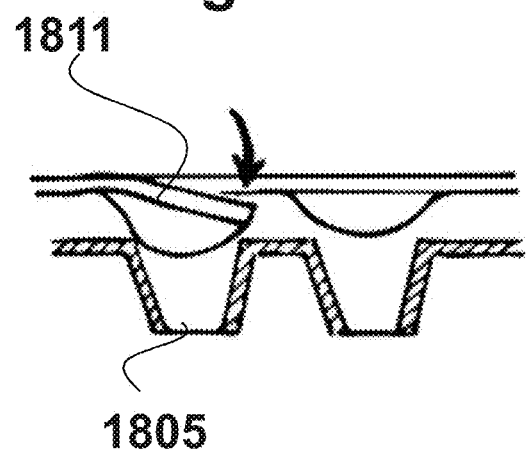

Although the sealing portions of the reflux valve may take any suitable form such that a fluid seal may be made between the outlet of a suction port tube and the interior of the manifold body, in many embodiments, the sealing portions may be configured to have a spherical geometry (e.g., a domed aspect) on the side of the sealing portion that engages the outlet of the suction port tube, as shown in FIG. 18D. Regardless of the design of the sealing portion (1811), the sealing portion is allowed to pivot or flex relative to the outlet (1805), such that when suction is applied through a vacuum inlet while penetrating the manifold body, the sealing portions pivot relative to the outlet and allow biota to pass through the suction port tubes and through the manifold body.

Figure 19:
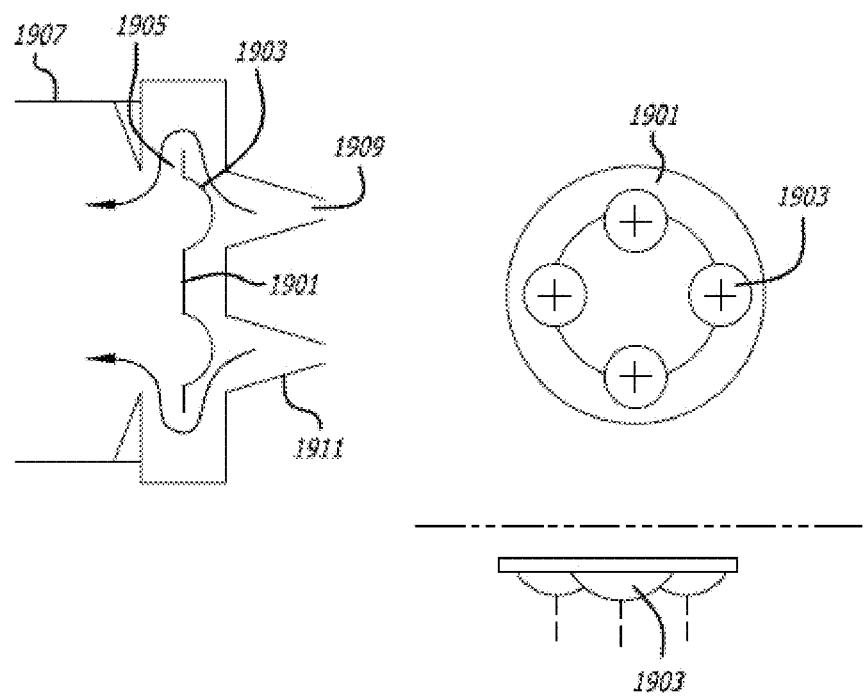
FIG. 19 provides schematic cross-sectional, top and side views of a floating reflux valve in accordance with embodiments.

Although specific embodiments of a reflux valve are provided in FIG. 18 in which sealing portions are securely engaged relative to the outlets of the suction port tubes via a support ring, it should be understood that many other configurations may be contemplated to provide similar backflow protection. In many configurations, as shown in FIG. 19, the reflux valve (1901) including sealing portions (1903) may float freely within a specified space (1905) of the manifold body (1907). In many such embodiments, when suction is applied, the reflux valve moves away from the suction port outlets (1909), allowing biota to pass from the suction port tubes (1911) through the manifold body and out through a vacuum outlet port (not shown). When suction ceases, the floating reflux valve (1901) assumes a position that causes the sealing portions (e.g., spherical or domes) to interface with the suction port tubes such that no residual biota existing in the manifold body can pass through the suction port tubes.

Figure 20:
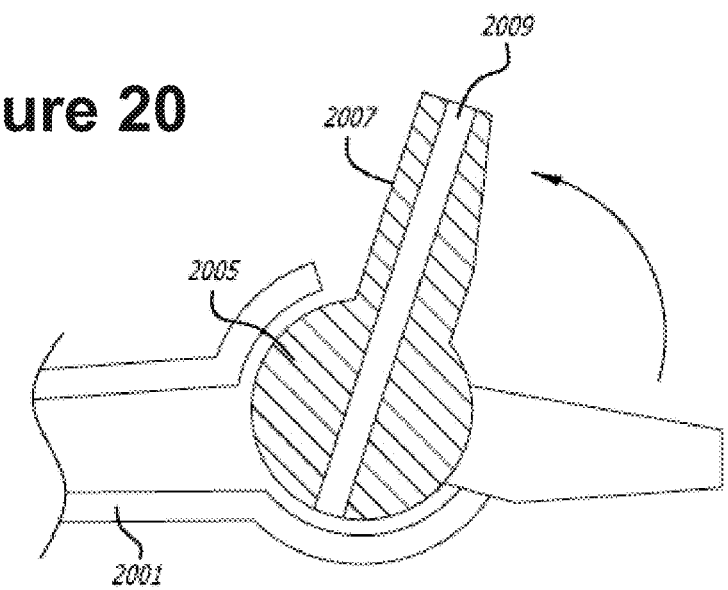
FIG. 20 provides a schematic cross-sectional view of a suction port tube valve in accordance with embodiments.

Although reflux valves for the prevention of backflow have been described, other mechanisms may be provided to prevent backflow. In many embodiments, as shown in FIG. 20, the proximal end (2001) of each possible suction port tube of the suction port assembly may take the form of a valve. In many such embodiments the proximal end incorporates a reciprocating valve body (2005) comprising a cylindrical tube (2007) that is rotatable relative to the longitudinal axis of the proximal end of the suction port tube and that is configured to be cooperative with a patient suction tube (not shown). Within the rotatable cylindrical tube resides at least one hollow tube (2009) disposed coaxial with the longitudinal axis of the rotatable cylindrical tube such that then the cylindrical tube is rotated such that the hollow tube is not aligned with the longitudinal axis of the suction port tube, no substance can flow through the suction port tube. When the cylindrical tube is rotated such that the hollow tube aligns with the longitudinal axis of the suction port tube, then biota can pass through the suction port tube and into the manifold body. In addition, when the rotating cylindrical tube is not aligned, it may operate to reduce the ability of biota trapped within the manifold body to exit the suction port tube.

Figure 21A:
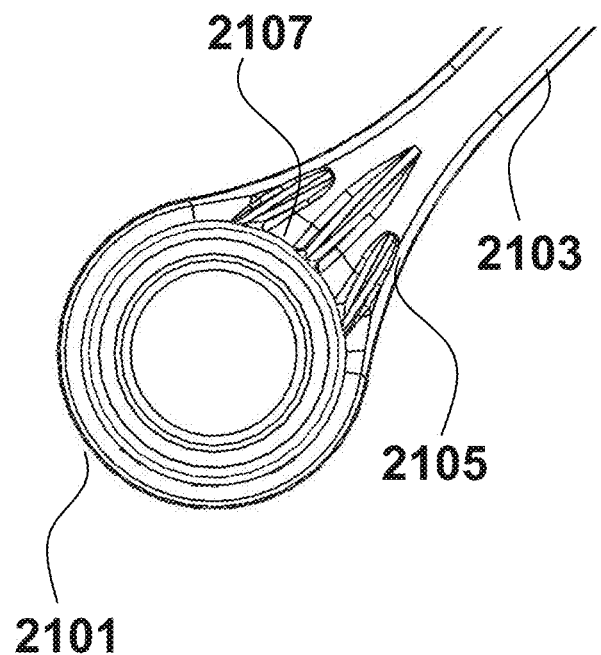
FIGS. 21A to 21C provide schematic perspective views of suction port tube caps in accordance with embodiments.
Figure 21B:
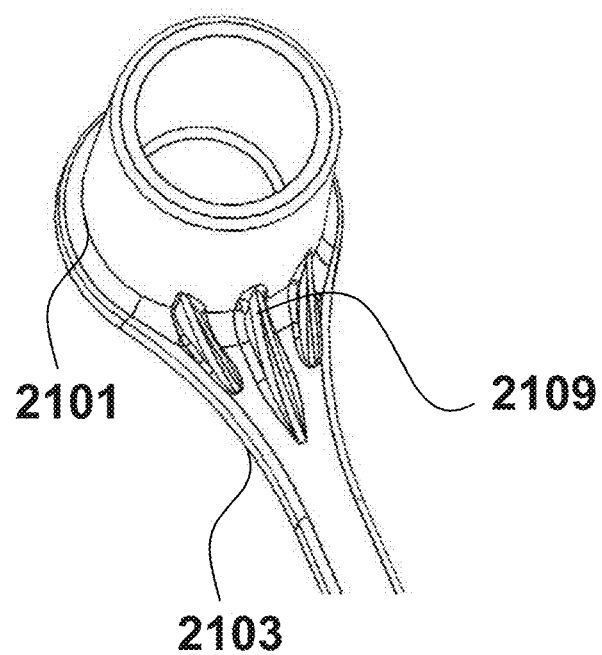
Figure 21C:
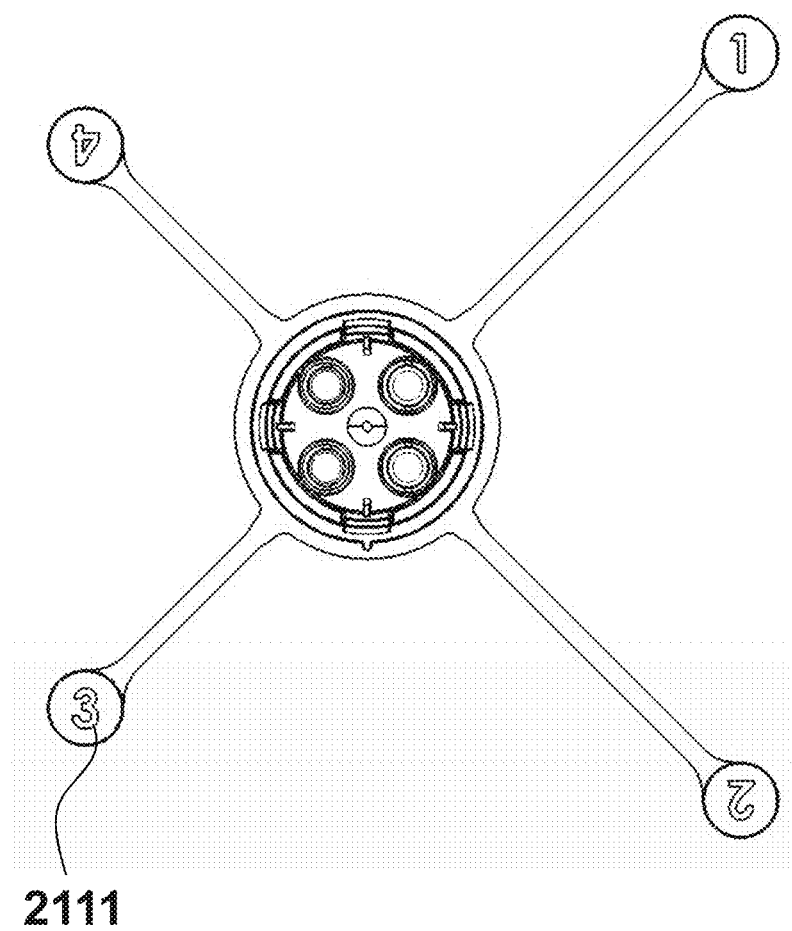

Although embodiments of caps to be used in association with the proximal ends (e.g., inlets) of the suction port tubes, it should be understood that these caps may incorporate a variety of features. As shown in FIGS. 21A to 21C, many embodiments of a cap (2101) capable of fitting onto the proximal end of a port tube may be fixed with a tether (2103). In some embodiments, a tether (2103) will have a base (2105) at the point of connection (2107) wider than the width of the remainder of the length of the tether. In other embodiments, a connection (2107) between a cap (2101) and a tether (2103) may be strengthened with one or more support gussets (2109) that bind a sidewall of the cap with the tether. In various such embodiments the caps may include identifiers (e.g., numbers) (2111) such that the associated suction port tubes may be distinguished one from the other when multiple suction port tubes are provided.

Figure 22A:
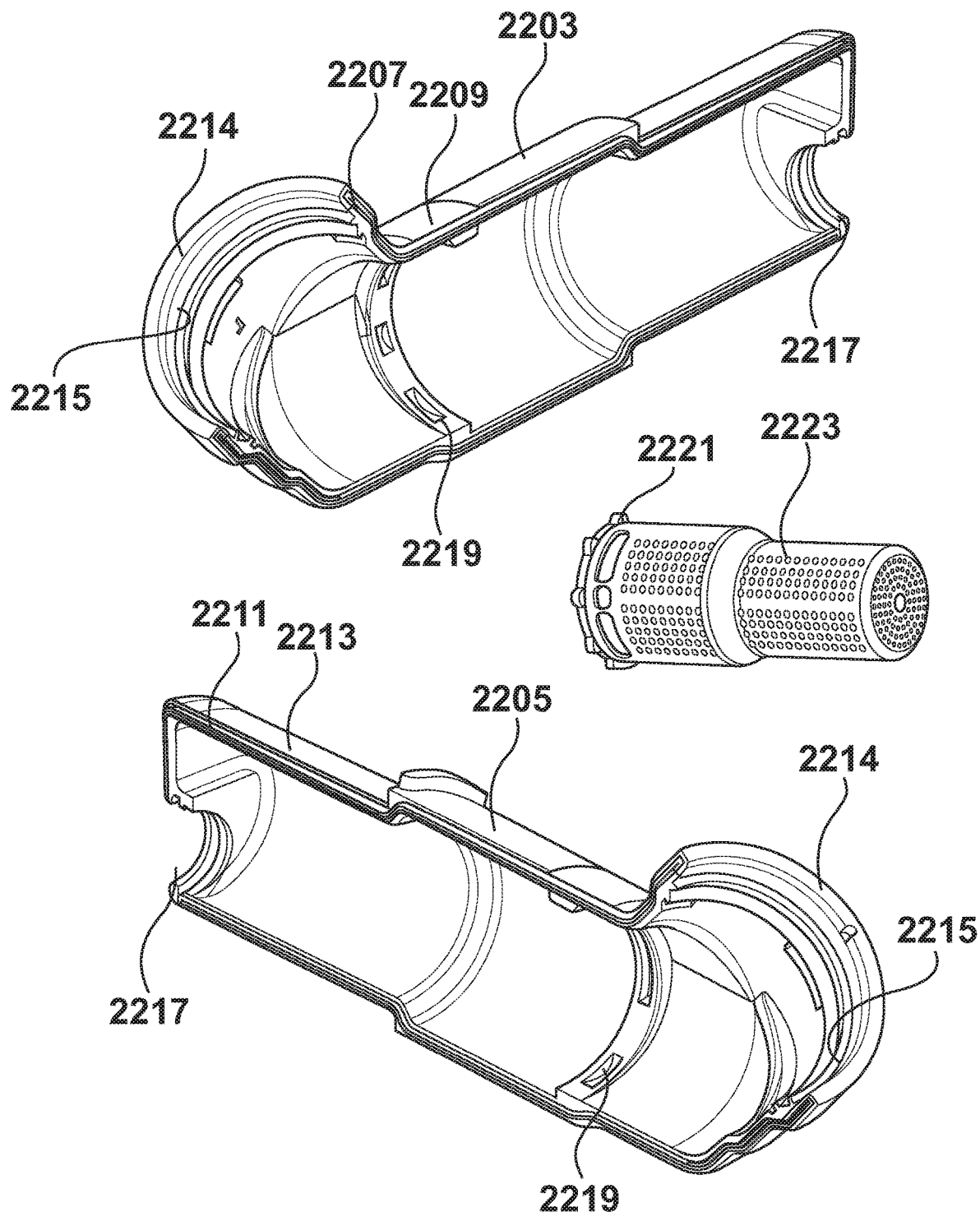
FIGS. 22A and 22B provide schematic perspective and cross-section views of weldable manifold casing halves in accordance with embodiments.
Figure 22B:
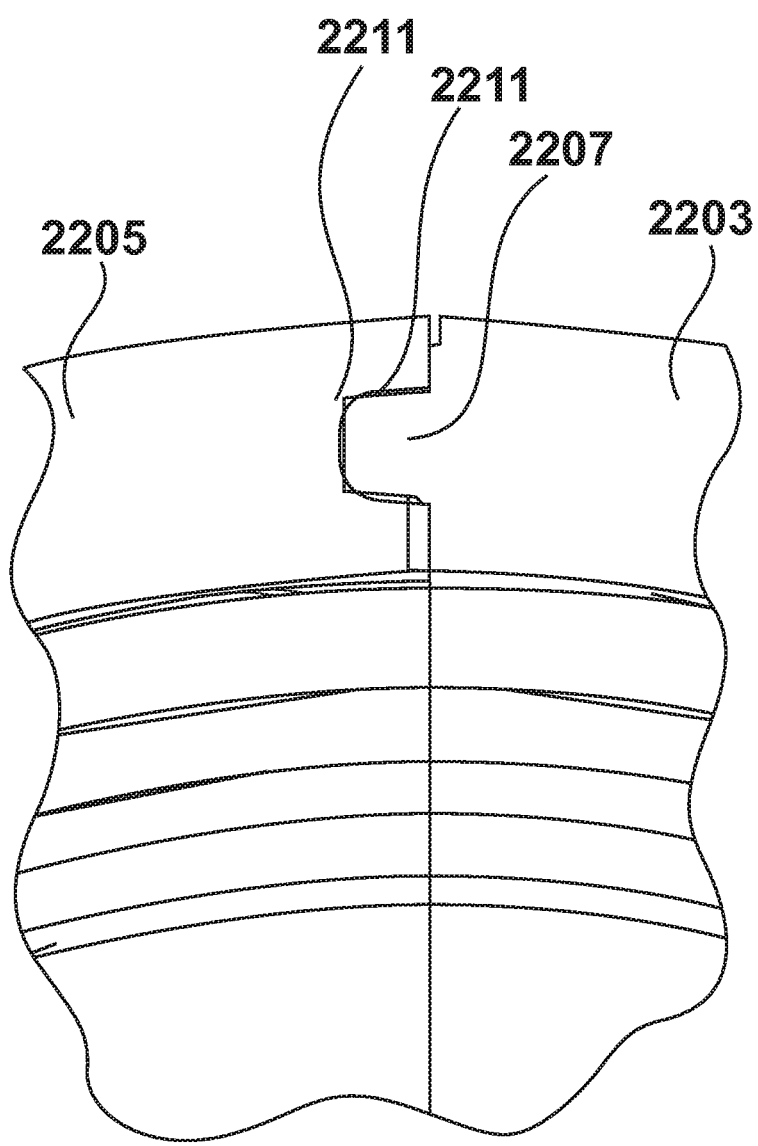
Figure 18D:
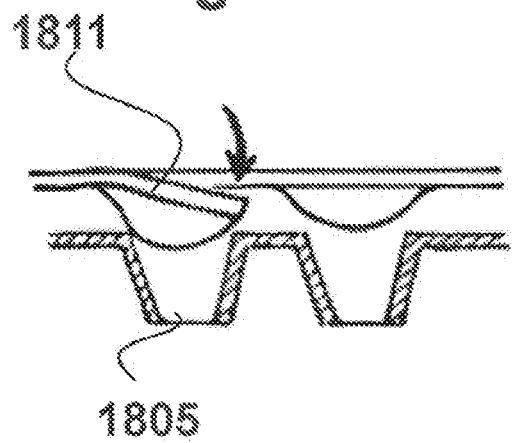

Embodiments are also directed to waste manifolds and methods of forming waste manifolds via a welding process. Exemplary embodiments of such waste-manifold assemblies are provided in FIGS. 22A and 22B. A basket having protrusions at the proximal end can be incorporated within a manifold body. In some such embodiments, a manifold body may be formed by welding together a first side outer casing (2203) with a second side outer casing (2205). Embodiments are directed to a first side outer casing (2203) having a tongue (2207) that extends along at least a portion of the first side edge (2209), and a second side outer casing (2205) that may have a cooperative groove (2211) that extends along a congruous portion of the second side edge (2213) such that a first side tongue (2207) can situate cooperatively in a second side groove (2211). Although in the pictured embodiments, the tongue (2207) is positioned on the left side of the manifold body and the groove (2211) on the right side, it should be understood that these configurations may be reversed, or the split between the two sides. A first side outer casing (2203) and a second side outer casing (2205) may leave a proximal opening (2214) capable of receiving a suction port assembly (not shown) and a circumferential groove (2215) adjacent the proximal opening capable of receiving a sealing element (e.g., O-ring). In addition, or in the alternative, the halves of an outer casing may leave a distal opening (2217) capable of receiving a valve body (not shown). Indentations (2219) disposed on the interior walls of one or both the first side outer casing (2203) and/or a second side outer casing (2205) may be configured to cooperatively engage protrusions (2221) on a filter element (2223) that may be situate within the interior of the manifold body. Although a filter basket is shown in FIG. 22A, in alternative embodiments, a disc or another device capable of capturing solid or semi-solid waste may be situated within the manifold body. In many embodiments of such weld joints, as shown in FIG. 22B, the tongue (2207) is configured such that when engaged within the groove (2211) at least a portion thereof (e.g., edge) (2225) bites into the body of the groove containing outer casing (2205) to thus ensure a fluid tight seal is formed therebetween.

Although specific embodiments have been described it should be understood that other features may be included with the waste manifold herein described. In many embodiments, an RFID (radio frequency identification device) or Bluetooth device may be incorporated into the manifold. In such embodiments the RFID/Bluetooth device can serve as a functional modifier of the manifold status (open vs. closed in the presence of an RFID/Bluetooth signal). Another function of the RFID/Bluetooth feature is to program vacuum settings for the procedure and/or device being inserted. Also, the RFID/Bluetooth feature can prevent unauthorized devices from being used with the vacuum device. In various embodiments, the vacuum port valve may be actively controlled by an RFID/Bluetooth device such that the vacuum port valve is open in proximity to the RFID/Bluetooth signal generator and the vacuum port valve is closed when no or insufficient signal is sensed. In an alternative embodiment, the vacuum port valve contains a magnetic component that may be configured to be attracted to the vacuum inlet of the vacuum device to enable vacuum port valve sealing and/or closure. In yet another alternative embodiment, the magnetic component in the vacuum port valve may be repelled by the vacuum inlet to enable valve opening.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A manifold for connection to a waste collection vacuum device, comprising:
    a manifold body having a proximal-most end and a distal end and defining an internal volume providing a fluid path therebetween, and wherein the manifold body has an angular bend disposed along a length thereof, such that the proximal-most end lies along a first longitudinal axis and the distal end lies along a second longitudinal axis, and wherein the first and second longitudinal axes are angularly offset;
    a suction port assembly disposed within the proximal-most end of the manifold body, and providing at least one suction port providing a fluid path into the internal volume of the manifold body;
    a vacuum port disposed within the distal end of the manifold body, and providing at least one fluid outlet from the internal volume of the manifold body, the vacuum port being configured to receive a vacuum inlet integral with the vacuum device;
    a filter element secured within the internal volume of the manifold body such that the fluid path between the proximal-most and distal ends passes therethrough;
    at least one orientation feature disposed on an outer surface of the manifold body and configured to affix the manifold body within the vacuum device and fix the orientation of the manifold body relative to the vacuum device; and
    wherein the manifold body and at least one orientation feature are configured such that when the manifold body is affixed within the vacuum device the at least one suction port disposed in the proximal-most end of the manifold body is angled upward relative to the direction of gravity.

2. The manifold of claim 1, wherein the angular offset is greater than 25° and less than 90°.

3. The manifold of claim 2, wherein the angular bend is greater than 30° and less than 60°.

4. The manifold of claim 3, wherein the angular bend is about 45°.

5. The manifold of claim 1, wherein the angular bend offsets the suction port from the fluid path disposed along the second longitudinal axis of the manifold body sufficiently to prevent reflux of a liquid waste back through the suction port.

6. The manifold of claim 1, wherein the filter element is a basket disposed along the second longitudinal axis and containing a plurality of apertures having at least a first aperture dimension, the plurality of apertures forming a portion of the fluid path through the manifold body.

7. The manifold of claim 6, wherein the basket has at least one overflow-relief aperture having a second aperture dimension larger than the at least first aperture dimension, the overflow-relief aperture being positioned adjacent to the top of the manifold body when the manifold body is affixed within the vacuum device.

8. The manifold of claim 6, wherein the basket has a plurality of apertures of at least two different aperture dimensions, and wherein the apertures disposed proximally along the basket have a larger aperture dimension than the apertures disposed distally along the basket.

9. The manifold of claim 6, wherein the basket has at least one protrusion disposed around a circumference thereof configured to cooperatively engage with at least one indentation disposed within an inner wall of the manifold body to affix the basket therein.

10. The manifold of claim 9, wherein the at least one protrusion uniquely orients the basket within the manifold body when coupled with the at least one cooperative indentation.

11. The manifold of claim 1, wherein the proximal-most end of the at least one suction port is configured to mate with a suction tube.

12. The manifold of claim 1, wherein the suction port assembly comprises a plurality of suction ports.

13. The manifold of claim 1, wherein the suction port assembly further comprises a sealing element configured to provide a fluid seal between the suction port assembly and the proximal-most end of the manifold body.

14. The manifold of claim 1, wherein the suction port assembly further comprises at least one mechanical lock configured to securely interconnect the suction port assembly with the proximal-most end of the manifold body.

15. The manifold of claim 1, wherein the suction port assembly comprises at least two suction ports, and wherein the at least two suction ports have distal outlets that extend within the internal volume of the manifold body, and wherein at least one suction port distally extends further within the manifold body than at least one other suction port.

16. The manifold of claim 15, wherein a variation of distal extension of the at least two suction ports is configured to reduce turbulence of a flow of fluid into the internal volume through the suction ports.

17. The manifold of claim 1, wherein two suction ports are disposed as upper suction ports and two suction ports are disposed as lower suction ports, such that the upper suction ports are positioned above the lower suction ports relative to the direction of gravity when the manifold body is affixed within the vacuum device.

18. The manifold of claim 17, wherein the distal ends of the upper suction ports are longer than the distal ends of the lower suction ports, and wherein a distance that the distal ends of the lower suction ports extend within the internal volume is configured such that the distal ends are disposed above a lowest portion of an overflow aperture disposed within the filter element, and such that reflux of waste through outlets of suction tubes is prevented.

19. The manifold of claim 1, wherein a portion of the manifold body including the angular bend has a substantially circular cross-section.

20. A manifold for connection to a waste collection vacuum device, comprising:
   a manifold body having proximal and distal ends and defining an internal volume providing a fluid path therebetween, and wherein the manifold body has an angular bend disposed along a length thereof, such that the proximal end lies along a first longitudinal axis and the distal end lies along a second longitudinal axis, and wherein the first and second longitudinal axes are angularly offset, wherein a portion of the manifold body including the angular bend has a substantially circular cross-section;
   a suction port assembly disposed within the proximal end of the manifold body, and providing at least one suction port providing a fluid path into the internal volume of the manifold body, wherein the angular bend is configured such that such that when the manifold body is affixed within the vacuum device the at least one suction port disposed in the proximal end of the manifold body is angled upward relative to the direction of gravity;
   a vacuum port disposed within the distal end of the manifold body, and providing at least one fluid outlet from the internal volume of the manifold body, the vacuum port being configured to receive a vacuum inlet integral with the vacuum device; and
   a filter element secured within the internal volume of the manifold body such that the fluid path between the proximal and distal ends passes therethrough.

* * * * *